(12) United States Patent
Mollicone et al.

(10) Patent No.: US 8,568,330 B2
(45) Date of Patent: Oct. 29, 2013

(54) COMPOSITE HUMAN PHYSIOLOGICAL STRESS INDEX BASED ON HEART BEAT AND SLEEP AND/OR ACTIVITY HISTORY DATA INCLUDING ACTIGRAPHY

(75) Inventors: Daniel J. Mollicone, Philadelphia, PA (US); Christopher G. Mott, Seattle, WA (US); Kevin Gar Wah Kan, Philadelphia, PA (US)

(73) Assignee: Pulsaw Informatics, Inc., Philadelphia, PA (US)

( * ) Notice: Subject to any disclaimer, the term of this patent is extended or adjusted under 35 U.S.C. 154(b) by 0 days.

(21) Appl. No.: 13/415,833

(22) Filed: Mar. 8, 2012

(65) Prior Publication Data

US 2012/0232414 A1    Sep. 13, 2012

Related U.S. Application Data

(60) Provisional application No. 61/450,551, filed on Mar. 8, 2011.

(51) Int. Cl.
*A61B 5/02* (2006.01)
(52) U.S. Cl.
USPC ........................................................ 600/508
(58) Field of Classification Search
USPC .................. 600/508, 301, 544, 546
See application file for complete search history.

(56) References Cited

U.S. PATENT DOCUMENTS

| | | | |
|---|---|---|---|
| 4,724,845 A | 2/1988 | Callahan | |
| 4,862,361 A | 8/1989 | Gordon et al. | |
| 5,433,223 A | 7/1995 | Moore-Ede et al. | |
| 5,682,882 A | 11/1997 | Lieberman | |
| 5,902,250 A | 5/1999 | Verrier et al. | |
| 6,443,904 B2 | 9/2002 | Nissilae | |
| 6,496,724 B1 | 12/2002 | Levendowsky et al. | |
| 6,511,424 B1 | 1/2003 | Moore-Ede et al. | |
| 6,516,222 B2 | 2/2003 | Fukuda | |
| 6,579,233 B2 | 6/2003 | Hursh | |
| 7,062,313 B2 | 6/2006 | Nissilae | |
| 7,189,204 B2 | 3/2007 | Ni et al. | |
| 7,376,457 B2 | 5/2008 | Ross | |
| 7,460,899 B2 | 12/2008 | Almen | |
| 7,824,888 B2 | 11/2010 | Kondo | |
| 7,860,561 B1 | 12/2010 | Modarres | |
| 8,083,682 B2 | 12/2011 | Dalal et al. | |
| 2010/0145219 A1* | 6/2010 | Grey | 600/546 |
| 2011/0125046 A1* | 5/2011 | Burton et al. | 600/544 |
| 2012/0071731 A1* | 3/2012 | Gottesman | 600/301 |

OTHER PUBLICATIONS

M.A. Cohen & A. Taylor, "Short-term cardiovascular oscillations in man: measuring and modelling the physiologies," 542.3 Jnl. of Physiol., 669-683 (2002 The Physiological Socy.).

(Continued)

*Primary Examiner* — Robert N Wieland
(74) *Attorney, Agent, or Firm* — Damian M. Biondo, Esq.

(57) ABSTRACT

Systems and methods are provided for providing a composite stress index representing a quantified stress level that an individual may be experiencing or may have experienced during a time interval of interest. The composite stress index is determined based on a combination of heart beat data representative of cardiac activity of the individual during the time interval of interest and one or both of: sleep history data comprising one or more sleep onset times and one or more awakening times during the time interval of interest; and physical activity history data representative of gross motor activity of the individual during the time interval of interest.

44 Claims, 8 Drawing Sheets

(56) References Cited

OTHER PUBLICATIONS

Gary G. Bernston and John T. Cacioppo, et al., "Heart Rate Variability: Stress and Psychiatric Conditions," Dynamic Electrocardiography 57-64 (2004).
D.C. Lin and R.L. Hughson, "Modeling Heart Rate Variability in Healthy Humans: A Turbulence Analogy," 86:8 Physical Review Letters 1650-1653 (Feb. 19, 2004).
Judith Orasanu, et al., "Physiological Monitoring of Team and Task Stressors," in J. Caldwell and J. McConnell (Eds.), Proceedings of the Biomonitoring for Physiological and Cognitive Performance during Military Operations Conference, SPIE Defense & Security Symposium, Orlando, FL, Mar. 28-Apr. 1, 2005.
Shigeki Shibata, "Cascade Model of Ventricular-Arterial Coupling and Arterial-Cardiac Baroflex Function for Cardiovascular Variability in Humans," 291 Am. J. Physiol. Heart Circ. Physiol. H2142-H2151 (Jun. 9, 2006).
B.J. West, et al., "Fractal Fluctuations in Cardiac Time Series," 270 Physica A 552-566 (Elsevier 1999).
Yoshiharu Yamamoto, et al., "Autonomic Control of Heart Rate During Exercise Studied by Heart Rate Variability Spectral Analysis," 71:3 J. App. Physiol. 1136-1142 (Sep. 1, 1991).
Yoshiharu Yamamoto, Richard L. Hughson, and Yoshio Nakamura, "Autonomic Nervous System Responses to Exercise in Relation to Ventilatory Threshold," 101 Chest 206S-210S (1992).
Yoshiharu Yamamoto, et al, "On the Fractal Nature of Heart Rate Variability in Humans: Effects of Vagal Blockade," 269:4 Am J. Physiol.: Regu. Physiol. R830-R837 (Oct. 1, 1995).
Marcus W. Angelink, et al., "Relationship Between Major Depression and Heart Rate Variability: Clinical Consequences and Implications for Antidepressive Treatment," 113 Psychiatry Res. 139-149 (Elsevier Sci. Ireland Ltd. 2002).
Deane E. Atkins, et al. "Sleep-Based Heart Period Variability in Panic Disorder with and without Nocturnal Panic Attacks," 22 Jnl. of Anxiety Disorders 453-463 (Elsevier Ltd. 2007).
Michael H. Bonnet, et al., "Hyperarousal and Insomnia: State of the Science," 14 Sleep Medicine Reviews 9-15 (Elsevier Ltd. 2009/2010).
M. H. Bonnet and D. L. Arand, "Heart Rate Variability in Insomniacs and Matched Normal Sleepers," 60 Psychosomatic Med. 610-615 (Am. Psych. Soc'y 1998).
Yoichi Chida and Mark Hamer, "Chronic Psychosocial Factors and Acute Physiological Responses to Laboratory-Induced Stress in Healthy Populations: A Quantitative Review of 30 Years of Investigations," 134:6 Psychological Bulletin 829-885 (Am. Pscyhological Assoc. 2008).
George P. Chrousos and Philip W. Gold, "The Concepts of Stress and Stress System Disorders," 267:9 JAMA 1244-1252 (JAMA Mar. 4, 1992).
Hagit Cohen, et al. "Power Spectral Analysis of Heart Rate Variability in Posttraumatic Stress Disorder Patients," 41 Biol. Psychiatry 627-629 (Soc'y for Biol. Psychiatry 1997).
Hagit Cohen, et al., "Autonomic Dysregulation in Panic Disorder and in Post-Traumatic Stress Disorder: Application of Power Spectrum Analysis of Heart Rate Variability at Rest and in Response to Recollection of Trauma or Panic Attacks," 96 Psychiatry Res. 1-13 (Elsevier Sci. Ireland 2000).
Su-Chang Fang, et al., "Heart Rate Variability and Daytime Functioning in Insomniacs and Normal Sleepers: Preliminary Results," 65 Jnl. of Psychosomatic Res. 23-30 (Elsevier Inc. 2008).
Niamh Flynn and Jack E. James, "Relative Effects of Demand and Control on Task-Related Cardiovascular Reactivity, Task Perceptions, Performance Accuracy, and Mood," 72 Int'l Jnl. of Psychophysiology 217-227 (Elsevier B.V. 2008).
Bruce H. Friedman and Julian F. Thayer, "Autonomic Balance Revisited: Panic Anxiety and Heart Rate Variability," 44:1 Jnl. of Psychosomatic Res. 133-151 (Elsevier Sci. Inc. 1998).
Martica Hall, et al., "Acute Stress Effects Heart Rate Variability During Sleep," 66 Psychosomatic Medicine 56-62 (Am. Psychol. Soc'y 2004).
Stephen N. Haynes, et al., "The Effects of Pre-sleep Stress on Sleep-Onset Insomnia," 90:6 Jnl. of Abnormal Psychology 601-606 (Am. Psychological Ass'n 1981).
J. Allen Herd, "Cardiovascular Response to Stress," 71:1 Physiological Reviews 305-330 (Am. Psychological Soc'y Jan. 1991).
F. Jurysta, et al., "The Impact of Chronic Primary Insomnia on the Heart Rate: EEG Variability Link," 120 Clinical Neurophysiology 1054-1060 (Elsevier Ireland Ltd. 2009).
Kathleen A. Lawler, "Cardiovascular and Electrodermal Response Patterns in Heart Rate Reactive Individuals During Psychological Stress," (The Soc'y for Psychphysiological Res., Inc. 1980).
Massimo Pagani, et al., "Sympathovagal Interaction During Mental Stress: A Study Using Spectral Analysis of Heart Rate Variability in Healthy Control Subjects and Patients with a Prior Myocardial Infarction," 83:4 Circulation II43-II51 (Instituto Richerche Cardiovascular, CRN, Milan, Italy 1991).
Madelon L. Peters, et al., "Cardiovascular and Endocrine Responses to Experimental Stress: Effects of Mental Effort and Controllability," 23:1 Psychoneuroendocrinology 1-17 (Elsevier Sci. Ltd. 1998).
Emilia Sforza, et al., "Cardiac Variability and Heart-Rate Increment as a Marker of Sleep Fragmentation in Patients with a Sleep Disorder: A Preliminary Study," 30:1 Sleep 43-51 (Assoc'd Professional Sleep Socy's, LLC 2007).
Andrew Steptoe, et al., "Control Over Work Pace, Job Strain and Cardiovascular Responses in Middle-aged Men," 11 Jnl. of Hypertension 751-759 (1993).
Juilian Thayer, et al., "Autonomic Characteristics of Generalized Anxiety Disorder & Worry," 39 Biol. Psychiatry 255-266 (Soc'y Biol. Psychiatry 1996).
Yvonne Iran, et al., "The Relationship Between Spectral Changes in Heart Rate Variability and Fatigue," 23:3 Jnl. of Psychophysiology (Hogrefer Pub. 2009).
Tanja G.M. Vrijkotte, et al., "Effects of Work Stress on Ambulatory Blood Pressure, Heart Rate, and Heart Rate Variability," (Am. Heart Assoc., Inc. 2000).
Lana L. Watkins, et al., "Association of Anxiety with Reduced Baroflex Cardiac Control in Patients After Acute Myocardial Infarction," 143:3 Am. Heart Jnl. (Elsevier Inc. Mar. 2002).
Amanda L. Wheat and Kevin T. Larkin, "Biofeedback of Heart Rate Variability and Related Physiology: A Critical Review," 35 Appl. Psychophysiological Biofeedback 229-242 (Springer 2010).
Vikram Kumar, et al., "Diminished Chaos of Heart Rate Time Series in Patients with Major Depression," 51 Biol. Psychiatry 733-44 (Soc'y of Biol. Psychiatry 2002).
Martica Hall, et al., "Symptoms of Stress and Depression as Correlates of Sleep in Primary Insomnia," 62 Psychosomatic Med. 227-230 (Am. Psychosomatic Soc'y 2000).
Stephen N. Haynes, et al., "The Effects of Presleep Stress on Sleep-Onset Insomnia," 90:6 Jnl. of Abnormal Psychology 601-606 (Am. Psychol. Ass'n Inc. 1981).
E. Shevy Healey, et al., "Onset of Insomnia: Role of Life-Stress Events," 43:5 Psychosomatic Medicine (Am. Psychosomatic Soc'y Inc. 1981).
Steven J. Linton, "Does Work Stress Predict Insomnia?: A Predictive Study," 9 Brit. Jnl. of Health Psychol. 127-136 (The Brit. Psychol. Soc'y 2004).
Charles M. Morin, et al., "Role of Stress, Arousal, and Coping Skills in Primary Insomnia," 65 Psychosomatic Med. 259-267 (Lippincott Williams & Wilkins 2003).
Atsuhiko Ota, et al., "Association Between Psychosocial Job Characteristics and Insomnia: An Investigation Using Two Relevant Job Stress Models—The Demand-Control-Support (DCS) Model and the Effort-Reward Imbalance (ERI) Model," 6 Sleep Med. 353-358 (Elsevier B.V. 2006).
Michael J. Sateia, et al., "Evaluation of Chronic Insomnia," 23:2 Sleep 1-66 (Am. Acad. of Sleep Med. 2000).
Alexandros N. Vgontzas, et al., "Chronic Insomnia and Activity of the Stress System: A Preliminary Study," 45:1 Jnl. of Psychosomatic Res. 21-31 (Elsevier Sci. Inc. 1998).
William F. Waters, et al., "Attention, Stress an Negative Emotion in Persistent Sleep-Onset and Sleep-Maintenance Insomnia," 16:2 Sleep 128-136 (Am. Sleep Disorders Assoc. & Sleep Res. Soc'y 1993).

(56) References Cited

OTHER PUBLICATIONS

Unpublished document re the "Beck Anxiety Inventory".

Wayne G. Whitehouse, et al., "Psychological and Immune Effects of Self-Hypnosis Training for Stress Management Throughout the First Semester of Medical School," 58 Psychosomatic Med. 249-263 (Am. Psychosomatic Soc'y 1996).

H. D. Critchley, et al., "Cerebral Correlates of Autonomic Cardiovascular Arousal: A Functional Neuroimaging Investigation in Humans," 523:1 Jnl. of Physiology 259-270 (The Physiology Soc'y 2000).

Diego A. Pizzagalli, et al., "Increased Percieved Stress is Associated with Blunted Hedonic Capacity: Potential Implications for Depression Research," 45 Behavior Res. and Therapy 2742-2753 (Elsevier Ltd. 2007).

Seward Smith and William W. Haythorn, "Effects of Compatibility, Crowding, Group Size, and Leadership Seniority on Stress, Anxiety, Hostility, and Annoyance in Isolated Groups," 22:1 Jnl. of Personality & Soc. Psych. 67-79 (Am. Psych. Ass'n 1972).

S.R. Tilton, "Review of the State-Trait Anxiety Inventory (STAI)," 3 page document, possibly unpublished, 48:2 NewsNotes 1-3 (NewsNotes 2008).

* cited by examiner

| TST (total wake time) | TIB (time in bed) | WASO (total wake after first sleep onset) |
|---|---|---|
| 6h | 7.2h | 2.75h |

| TST (total wake time) | TIB (time in bed) | WASO (total wake after first sleep onset) |
|---|---|---|
| 8.5h | 8.7h | 0.1h |

US 8,568,330 B2

COMPOSITE HUMAN PHYSIOLOGICAL STRESS INDEX BASED ON HEART BEAT AND SLEEP AND/OR ACTIVITY HISTORY DATA INCLUDING ACTIGRAPHY

RELATED APPLICATIONS

This application claims benefit of the priority of U.S. Provisional Patent Application No. 61/450,551, filed Mar. 8, 2011.

TECHNICAL FIELD

The invention relates quantifying human physiological stress. Particular embodiments provide methods and systems for quantifying human physiological stress based on heart beat data in combination with sleep history data and/or physical activity history data.

BACKGROUND

There is a general desire to reliably and objectively quantify the subjective experience of human physiological stress.

SUMMARY

One aspect of the invention provides a method for determining a composite stress index for an individual using a computer. The method comprises: providing sleep history data at a computer, the sleep history data comprising one or more sleep onset times and one or more awakening times for an individual during a time interval of interest; providing heart beat data at the computer, the heart beat data representative of the individual's cardiac activity during the time interval of interest; determining a quantitative composite stress index with the computer based at least in part on both the sleep history data and the heart beat data, the composite stress index representative of a general physiological stress of the individual during the time interval of interest.

Another aspect of the invention provides 201 a method for determining a composite stress index for an individual using a computer. The method comprises: providing physical activity history data at a computer, the physical activity history data representative of gross motor activity of the individual during a time interval of interest; providing heart beat data at the computer, the heart beat data representative of the individual's cardiac activity during the time interval of interest; and determining a quantitative composite stress index with the computer based at least in part on both the physical activity history data and the heart beat data, the composite stress index representative of a general physiological stress of the individual during the time interval of interest.

Another aspect of the invention provides a system for determining a composite stress index for an individual. The system comprises: an actigraphy sensor for providing actigraphy data regarding an individual during a time interval of interest; a heart beat sensor for providing heart beat data, the heart beat data representative of the individual's cardiac activity during the time interval of interest; and a controller, the controller configured to provide: a sleep estimator configured to determine sleep history data for the individual during the time period of interest based at least in part on the actigraphy data, the sleep history data comprising one or more sleep onset times and one or more awakening times for the individual during the time interval of interest; and a composite stress index estimator configured to determine a quantitative composite stress index for the individual based at least in part on both the sleep history data and the heart beat data, the composite stress index representative of a general physiological stress of the individual during the time interval of interest.

Another aspect of the invention provides a system for determining a composite stress index for an individual comprising: an actigraphy sensor for providing physical activity history data regarding an individual during a time interval of interest, the physical activity history data representative of gross motor activity of the individual during the time interval of interest; a heart beat sensor for providing heart beat data, the heart beat data representative of the individual's cardiac activity during the time interval of interest; and a controller configured to provide a composite stress index estimator, the composite stress index estimator configured to determine a quantitative composite stress index for the individual based at least in part on both the physical activity history data and the heart beat data, the composite stress index representative of a general physiological stress of the individual during the time interval of interest.

Other aspects of the invention provide computer program products comprising computer instructions which, when executed by a processor, cause the processor to carry out the methods of the invention.

Further details, features and aspect of particular embodiments are provided in the description below and in the drawings appended hereto.

BRIEF DESCRIPTION OF DRAWINGS

Exemplary embodiments are illustrated in referenced figures of the drawings. It is intended that the embodiments and figures disclosed herein are to be considered illustrative rather than restrictive.

In drawings which illustrate non-limiting embodiments.

DESCRIPTION

Figure 1A:
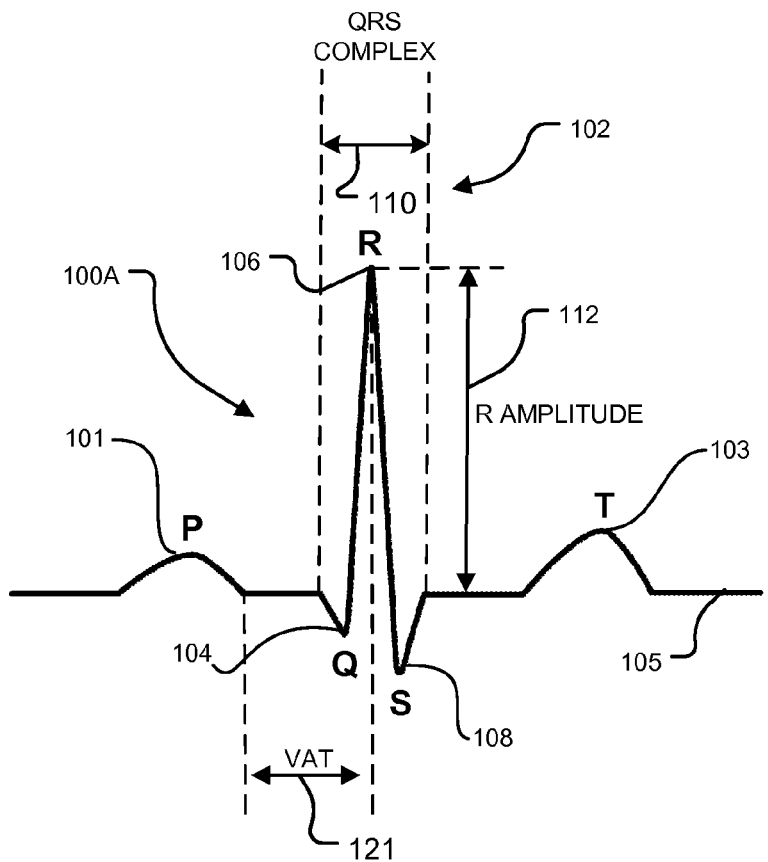
FIG. 1A illustrates a portion of an exemplary cardiac waveform which exhibits one QRS complex.

Before the embodiments of the invention are explained in detail, it is to be understood that the invention is not limited in its application to the details of construction and the arrangements of the operative components set forth in the following description or illustrated in the drawings. The invention is capable of other embodiments and of being practiced or being carried out in various ways. Also, it is understood that the phraseology and terminology used herein are for the purpose of description and should not be regarded as limiting. The use herein of "including" and "comprising", and variations thereof, is meant to encompass the items listed thereafter and equivalents thereof. Unless otherwise specifically stated, it is to be understood that steps in the methods described herein can be performed in varying sequences.

As will be described in more detail below, aspects of the invention provide systems and methods for quantifying a level of stress that an individual may be experiencing or may have experienced during a time interval of interest. The composite stress index is determined based on a combination of heart beat data representative of cardiac activity of the individual during the time interval of interest and one or both of: sleep history data comprising one or more sleep onset times and one or more awakening times during the time interval of interest; and physical activity history data representative of gross motor activity of the individual during the time interval of interest.

The term "stress" has numerous definitions applicable to different fields. Stress may be considered to refer to a general state of an individual as would be understood by a psychologist, physiologist, biologist or the like. Stress may comprise: a non-specific response of the body to a demand placed upon it; an effect that results when a demand is placed on an individual; and/or the like. Due, in part, to the non-specific meaning of the term "stress", there is corresponding lack of standardization with respect to methods for assessing an individual's stress level.

Stress may result in changes to an individual's physiology or behavior. Some aspects of the impact of stress on physiological or behavioral characteristics may be quantitatively measured, using sensors or other observational techniques. Some embodiments of the invention comprise determining a quantified index of an individual's stress level based on heart beat data in combination with one or more of: physical and sleep history data from the individual.

FIG. 1A illustrates a portion of a typical cardiac waveform 100A. More specifically, FIG. 1A illustrates a portion of a waveform 100A from a typical electrocardiogram (ECG), which plots the electrical impulse of the heart (typically measured as a voltage, e.g. mV) over time (typically in ms). Waveform 100A exhibits a number of characteristic features, including, by way of example, the P-wave 101, the QRS Complex 102, and the T wave 103. QRS Complex 102 includes a number of the deflections seen on the typical ECG waveform 100A and is usually the central and most visually obvious part of waveform 100A. QRS complex 102 corresponds to the depolarization of the right and left ventricles of the heart. Exemplary ECG waveform 100A shown in FIG. 1A has 5 deflections, typically referred to as the P, Q, R, S, and T waves. In some conditions, ECG waveforms also comprise a U wave, which is not illustrated in FIG. 1A. Q-wave 104 may be understood to be any downward deflection after P-wave 101. R-wave 106 may be understood to be an upward deflection after Q-wave 104, and S-wave 108 may be understood to be any downward deflection after R-wave 106. The Q, R and S waves 104, 106, 108 may occur in rapid succession, typically do not all appear in all ECG leads, and may correspond generally to a single event. The Q, R, and S waves 104, 106, 108 are frequently considered as a whole complex—the QRS complex 102.

As shown in FIG. 1A, a QRS duration 110 may be defined to be the total amount of time for QRS complex 102 to evolve—i.e., from the beginning of Q-wave 104 through R-wave 106 and to the end of the S-wave 108. An R-Amplitude 112 may be defined as the total voltage displacement from the peak of R wave 106 to a baseline level 105. The ventricular activation time (VAT) 121 may be defined as the elapsed time from the beginning of the Q-wave to the peak of the R-wave, and physically VAT 121 represents the time in which the ventricle depolarizes. The occurrence of R-wave 106 is commonly referred to as the primary 'heart beat' signal.

As used herein, heart beat data should be understood to comprise data representative of cardiac activity of an individual. Heart beat data may comprise: a time series ECG waveform, a sequence of times representative of the occurrences of R peaks, an average rate of R peaks, and/or other characteristics related to cardiac activity of an individual. Techniques used to measure heart beat data include without limitation: ECG holter monitors, blood pressure sensors, photoplethysmography sensors (PPG) or "pulse oximeters" and/or the like. A technique such as ECG monitoring may be considered superior in some circumstances because it provides a clear QRS waveform, while other techniques (such as PPG) that detect the timing of the R-peaks may still be used advantageously in some circumstances due to factors such as sensor unobtrusiveness. Some embodiments of the invention may involve the use of different types of heart beat data.

Figure 1B:
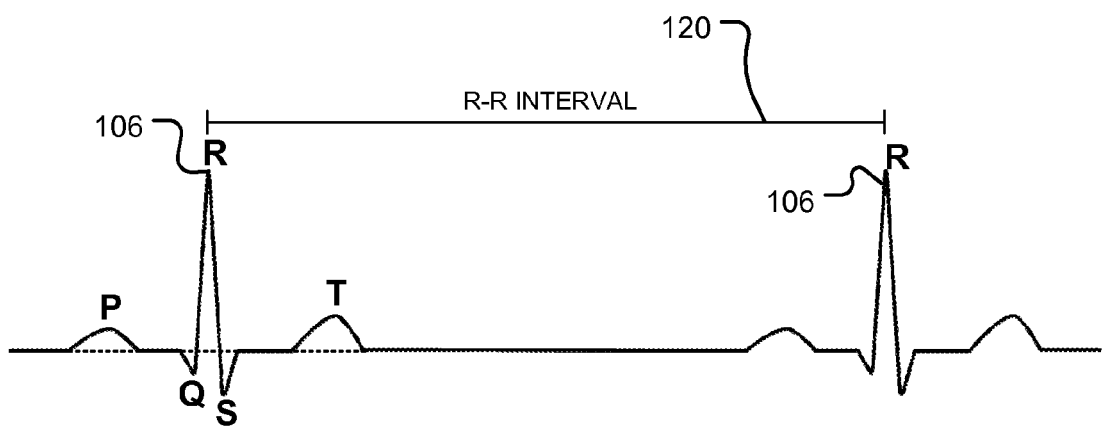
FIG. 1B illustrates a portion of a cardiac waveform which exhibits a pair of QRS complexes.

One characteristic of cardiac activity that may be considered part of an individual's heart beat data is the amount of time or the interval between successive R-waves. This interval may be referred to as the R-R interval and is shown in FIG. 1B as R-R interval 120. Another characteristic of an individual's cardiac activity that may be considered to be part of the individual's heart beast data, or may be inferred from other aspects of heart beat data, is the individual's heart rate (HR). Heart rate may be measured as the number of R waves occurring in a given time interval or an inverse of the average R-R interval over the given time interval.

Figure 2A:
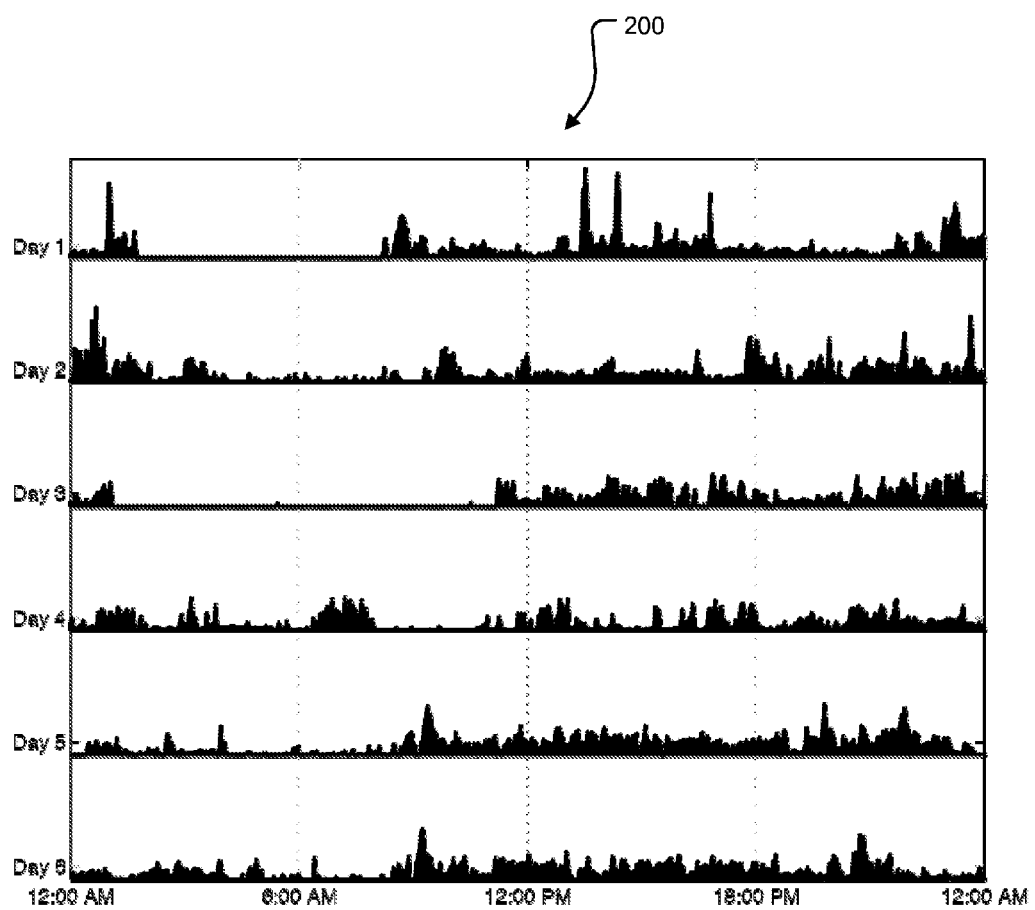
FIG. 2A provides an example of physical activity history data for an individual collected over a six day period.

FIG. 2A illustrates a sample of physical activity history data 200 for an individual. In the particular case of the FIG. 2A example, physical activity history data is measured by an actigraphy sensor over six consecutive days. Collecting physical activity history data may involve afixing an actigraphy sensor, (which may also be referred to as an "actimetry sensor", "actigraph", "motion sensor", and/or the like) to a location on the body of an individual. Locations for sensor position on the body may include, but are not limited to, the wrist, ankle, boot, and the like. An actigraphy sensor mounted on the body of an individual may be sensitive to motion caused by arm movements, walking, running, and other gross motor activities of the individual.

An actigraphy sensor measures the movements of a user's body typically (although not exclusively) by employing an accelerometer. In some actigraphy sensors, three orthogonally oriented accelerometers are coupled in such a manner as to detect body movement(s) in each of the three corresponding physical directions. Typical actigraphy sensors use the output of the accelerometers to generate so called "counts". By way of non-limiting example, such activity counts may be generated using zero crossings of accelerometer output, integration-type sampling of accelerometer output, or a suitable thresholding process. The activity count may then be stored in the actigraphy sensor's memory or in some other memory accessible to the sensor.

Activity counts detected by the actigraphy sensor are typically accumulated within time intervals which may be referred to as "epochs". Typically, an epoch may range between fractions of seconds to several minutes in duration. In some actigraphy sensors, the epoch length can be variably set by the user depending upon the device's application. One non-limiting example of an actigraphy sensor is the commercially available Philips® Actiwatch manufactured by Koninklijke Philips Electronics N.V. Other examples of actigraphy sensors are known to those of ordinary skill in the art.

As used herein, physical activity history data of an individual should be understood to comprise data representative of gross motor activity of the individual. Physical activity history data may include without limitation: a time series of activity counts, a sequence of times representative of physical activity, a rate of change of gross motor activity, translational motion rates, rotational motion rates, a set of discrete samples indicative of amplitudes of gross motor movement(s) and/or other characteristics related to gross motor movement(s) of the individual. Techniques used to measure physical activity history data include without limitation: wrist-worn actigraphy sensors, pedometers, heel-strike shoe sensors, accelerometers embedded in phones, accelerometers otherwise mounted or coupled to an individual's body and/or the like.

Figure 2B:
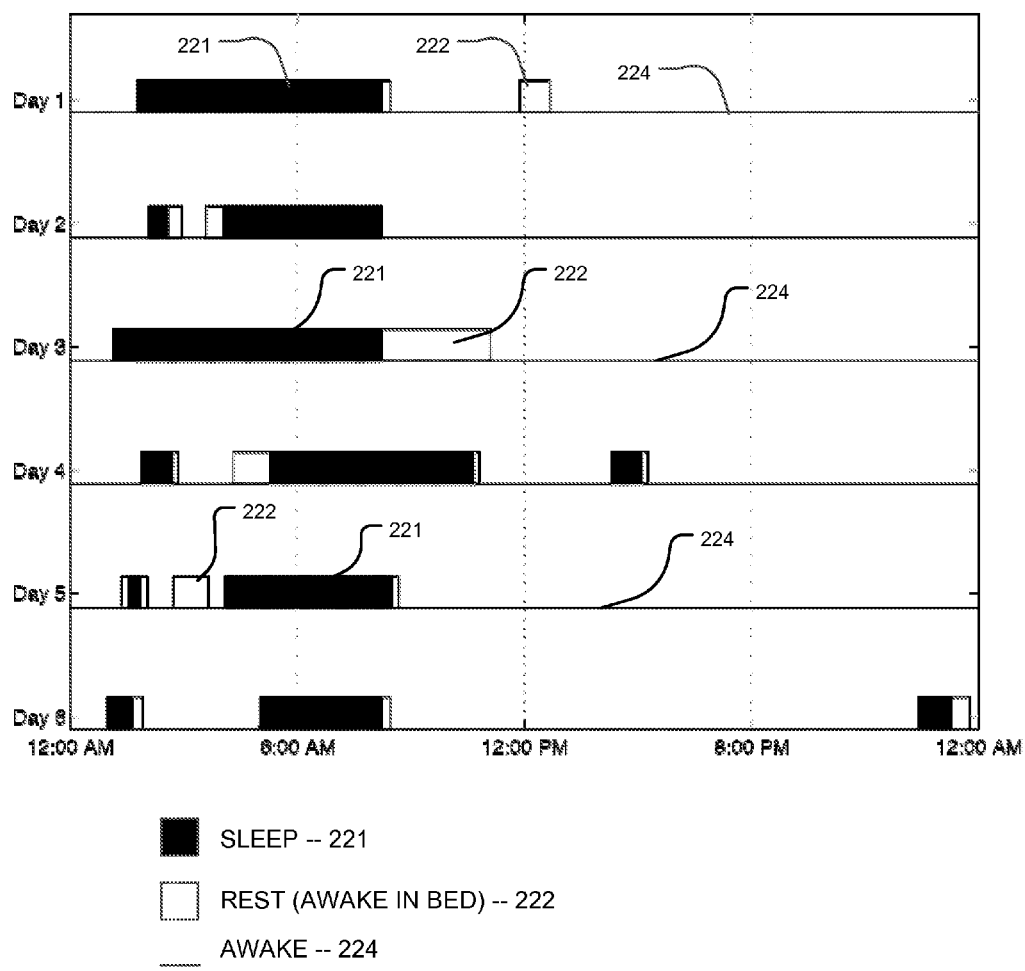
FIG. 2B provides a sample of sleep history data for an individual determined from the FIG. 2A physical activity history data over the same six day period.

FIG. 2B illustrates a sample of sleep history data 220 for an individual determined from the FIG. 2A physical activity history data 200 over the same six day period. Time periods in which the individual was asleep are shown as filled boxes 221, time periods in which the individual was awake but resting in bed are open boxes 222, and time periods in which the individual was awake but not in bed are lines 224. As used herein, sleep history data should be understood to comprise data representative of an individual's sleep state during a time period of interest. As shown by exemplary sleep history data 220 of FIG. 2B, sleep history data may comprise information about whether the individual is in a sleep state or an awake state at any given time during the time period of interest. Sleep history data may additionally or alternatively comprise: a set of sleep start times (sleep onset times) and end times (awakening times); a time series data set, wherein each data element comprises a time point and sleep/wake state classification; and/or the like. In some embodiments sleep/wake classifications states may be coded numerically (e.g. wake=0, sleep=1). Sleep/wake classifications used in the sleep history data are not limited to the binary states of sleep and awake. In particular embodiments, sleep history data may comprise sleep/wake classifications such as: asleep, awake, REM sleep, non-REM sleep, deep sleep, light sleep, in bed, awake in bed, sleeping in bed, and the like.

Figure 3:
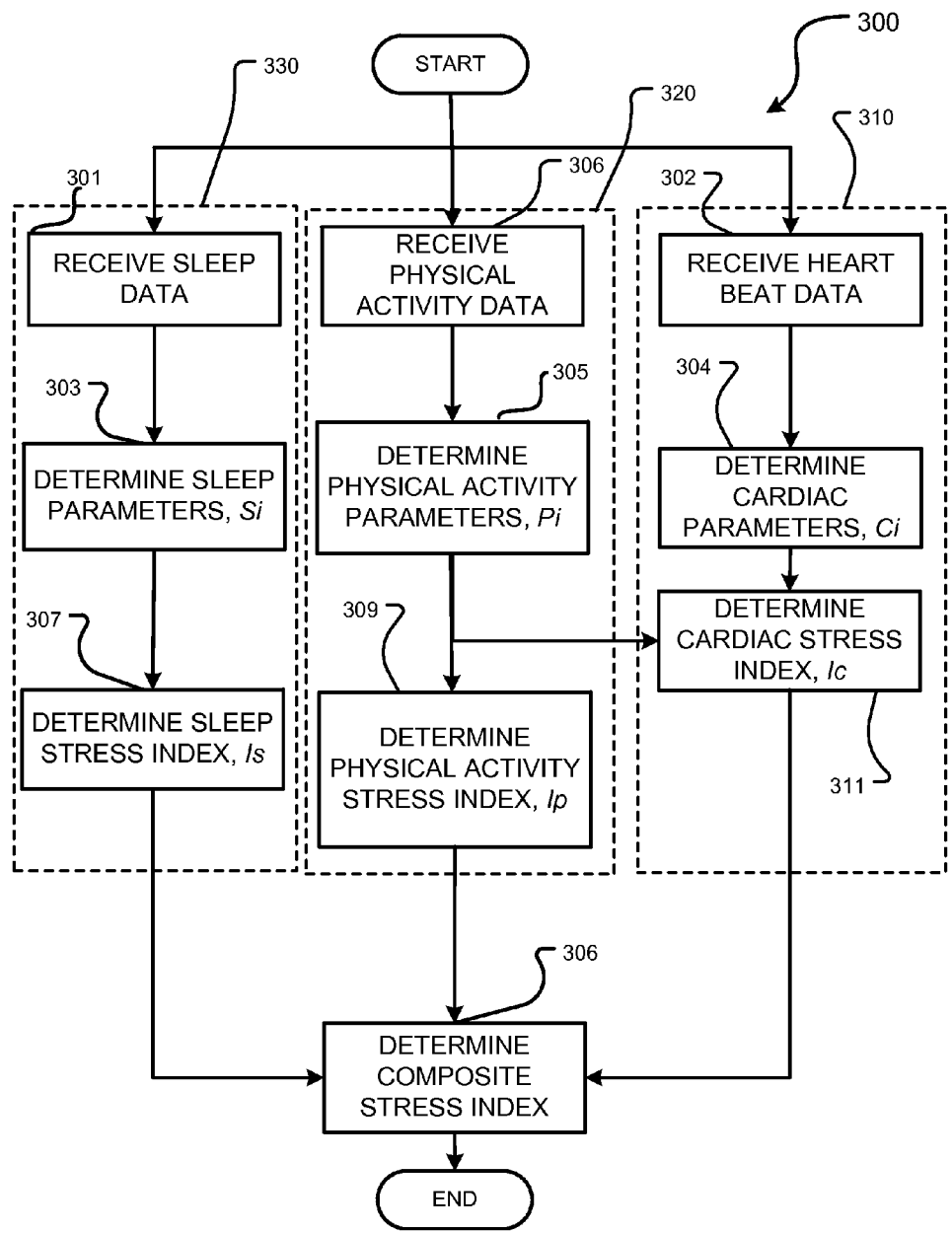
FIG. 3 is a flowchart illustrating a method for determining a composite stress index according to a particular embodiment.

FIG. 3 is a flowchart illustrating a method 300 for determining a composite stress index I in accordance with a particular embodiment. Method 300 may be implemented by a suitably configured computer, processor and/or the like (not shown). While any suitable hardware capable of executing software instructions may be used to implement method 300, the term computer is used herein to facilitate description without loss of generality. In the illustrated embodiment, method 300 involves processing heart beat data (in branch 310), physical activity history data (in branch 320) and sleep history data (in branch 330) to determine a composite stress index in block 306. In other embodiments, heart beat data (branch 310) can be combined with only sleep history data (branch 330) to determine the composite stress index in block 306. In other embodiments, heart beat data (branch 310) can be combined with only physical activity history data (branch 320) to determine the composite stress index in block 306. Method 300 may commence as a parallel process, although this is not necessary.

In the illustrated embodiment, block 302 (of branch 310) involves receiving heart beat data, block 306 (of branch 320) involves receiving physical activity history data and block 301 (of branch 330) involves receiving sleep history data. Heart beat data received in block 302 may come from a suitably configured cardiac/heart beat sensor of the type described herein. Physical activity history data received in block 306 may come from a suitably configured actigraphy sensor, motion sensor and/or the like. Sleep history data received in block 301 may be derived from physical activity history data received in block 306. More particularly, where physical activity history data received in block 306 comprises actigraphy data, sleep history data received in block 301 may be derived from such actigraphy data as described herein (see FIGS. 2A, 2B). Sleep history data received in block 301 may additionally or alternatively be received from an individual who may be interrogated as to their sleep history, from a sleep log kept by the individual and/or the like. Ultimately, it will be appreciated that there are many ways for receiving or otherwise procuring heart beat data (block 302), physical activity history data (block 306) and/or sleep history data (block 301) and particular embodiments of the invention may incorporate any suitable technique for receiving or otherwise procuring this data.

In the illustrated embodiment, the heart beat data received in block 302 (branch 310), the physical activity data received in block 306 (branch 320) and the sleep data received in block 301 (branch 330) all correspond to (or at least overlap) a time interval of interest for which method 300 is to be applied. However, the procedures involved in the receipt of data in blocks 302, 306 and 301 may be performed at different times. For example, receipt of heart beat data in block 302 may involve monitoring of ECG output over the time interval of interest and so the receipt of heart beat data in block 302 may occur in substantially real time during the time interval of interest. In contrast, the receipt of sleep history data in block 301 may come from a user entering data from a sleep log. While the sleep history data itself may overlap the time interval of interest, the actual receipt of the sleep history data in block 301 may occur well after the time interval of interest.

Starting in branch 301 at block 302, the heart beat data received in block 302 may originate from a suitably configured cardiac/heart beat sensor, such as any of the types described herein. Techniques for actually communicating the heart beat data in block 302 to the computer implementing method 300 may include, but are not limited to: receiving an electronic message over a communication network, reading files from a storage medium, accessing a database, receiving input from a user-input device; communication (directly or through suitable signal conditioning circuitry) to a heart beat sensor, and/or the like.

The block 302 heart beat data may then be used in block 304 to determine one or more cardiac parameters $C_i$. In some embodiments, each cardiac parameter $C_i$ determined in block 304 comprises a numerical value that summarizes or is otherwise representative of a corresponding characteristic of the block 302 heart beat data. A cardiac parameter $C_i$ determined in block 304 may be correlated with the stress of the individual whose heart beat data is received in block 302. In some embodiments, multiple cardiac parameters $C_i$ may be determined in block 304. In some embodiments, the block 302 heart beat data may be separated into multiple time segments or may otherwise comprise multiple time intervals of interest and block 304 may involve the determination of one or more corresponding cardiac parameters $C_i$ for each time segment/interval.

One cardiac parameter that may be determined in block 304 based on the block 302 heart beat data is heart rate ("HR"). As discussed above, determining HR may involve counting the number of R-waves (or other indicators of individual heart beats) occurring in a given time interval or inverting the average R-R period over the given time interval. HR is typically read over an extended interval, such as 3 minutes, 10 minutes, or half an hour, etc., but in some cases, for example, where wearable or otherwise portable heart beat sensors are used, the measurement interval can be much longer (e.g., 24 hours) Wearable heart rate monitors are readily available commercially.

Another exemplary cardiac parameter that may be determined in block 304 based on the block 302 heart beat data is heart-rate variability (HRV). HRV is a measure of the variation in the duration of the R-R interval (see R-R interval 120 of FIG. 1B), over time. For example, the time interval between heart beats (R-R interval 120) may vary even when the heart rate (HR) is otherwise constant across a longer timescale. In particular embodiments, HRV may be determined in block 304 to be the statistical variation of a set of R-R intervals 120.

HRV has been shown to be negatively correlated to arousal of the autonomic nervous system, which is a typical physiological stress response. Reductions in an individual's HRV (e.g. relative to an individual's baseline HRV or to a population average HRV) may be an indicator that the individual is experiencing higher stress levels.

Assuming that the block 302 heart beat data comprises or can be used to obtain a sequence of heart beat (R-R) intervals 120, block 304 may comprise any one or more of several techniques to determine HRV. The most widely used techniques for determining HRV can be grouped under time-domain and frequency-domain categories. Time-domain methods are based on measuring the duration of beat-to-beat (R-R) intervals, and then further analyzing the RR intervals to provide metrics:

SDNN, the standard deviation of R-R intervals, often calculated over a 24-hour period.
SDANN, the standard deviation of the average R-R intervals calculated over relatively short periods, usually 5 minutes. (SDANN is therefore a measure of changes in heart rate due to cycles longer than 5 minutes.)
RMSSD, the square root of the mean squared difference of successive R peaks.
NN50, the number of pairs of successive RRs that differ by more than 50 ms.
pNN50, the proportion of NN50 divided by total number of RRs.

Any of these time-domain-based HRV metrics may comprise cardiac parameters Ci of the type determined in block 304.

Several frequency-domain techniques may also be used in block 304 to determine a metric for HRV. In one exemplary technique, given a sequence of R-R intervals, a time series data set is first created representing the R-R interval durations. The frequency-domain power spectral density (PSD) of the R-R interval time series is then determined. The total power within a high frequency range, and the total power within a low frequency range may then be ascertained from the power spectral density, wherein each of the high and low frequency ranges is specified by an upper and lower frequency bound. In some embodiments, the high frequency range may be defined between an upper bound of 0.4 Hz and a lower bound of 0.15 Hz, and the low frequency range may be defined between an upper bound of 0.15 Hz and a lower bound of 0.04 Hz. The total power within a frequency range may be calculated by integrating the area under a curve of the power spectral density plot between the upper and lower frequency bounds. The ratio of the high frequency to low frequency power (HF/LF) is then determined and used as a HRV metric. Power spectral density (PSD), can be determined using parametric or nonparametric techniques, and provides basic information on the power distribution across frequencies. Commonly used techniques for determining the PSD of a time series comprise the discrete Fourier transform and variations thereof.

Another technique for determining an HRV metric in block 304 based on the block 302 heart beat data comprises the used of non-linear analysis of heart rate variability—e.g. in the form of a Poincaré plot. Data points representing pairs of successive R-R intervals are created and plotted on the Poincaré plot, with the x-axis representing the current R-R interval, and the y-axis representing the previous R-R interval. An HRV is quantified by fitting mathematically defined geometric shapes to the data. Other techniques which may be used in block 304 to determine HRV metrics comprise: the correlation dimension, nonlinear predictability, point-wise correlation dimension, and approximate entropy techniques.

It will be appreciated that there are a wide variety of techniques for determining different HRV metrics in block 304 based on the block 302 heart beat data. Systems and methods according to various embodiments can be tailored to utilize any one or more of these techniques and their corresponding HRV metrics. When referring to HRV or HRV metrics, it is understood that systems and methods according to various embodiments of the invention are designed to operate with such data regardless of how it is determined.

After determining one or more cardiac parameters $C_i$ in block 304, method 300 proceeds to block 311 which involves determining a cardiac stress index $I_c$ based at least in part on the one or more block 304 cardiac parameters $C_i$. The cardiac stress index $I_c$ determined in block 311 may also optionally be based on the block 305 physical activity parameters $P_i$ discussed in more detail below In accordance with some embodiments, determining the cardiac stress index $I_c$ in block 311 may comprise transforming one or more of the values of the block 304 cardiac parameters $C_i$ using a numeric transfer function.

In particular embodiments, determining the cardiac stress index $I_c$ in block 311 may comprise using a block 304 cardiac parameter $C_i$ as an index into a look-up table in which ranges of cardiac parameter values are associated with corresponding values for the cardiac stress index $I_c$. In other embodiments, determining the cardiac stress index $I_c$ in block 311 may comprise determining a difference metric between a value of a cardiac parameter $C_i$ determined in a time interval of interest and a reference cardiac parameter value, and, optionally, transforming the difference metric using a suitable transfer function. The reference cardiac parameter value may be determined using a variety of suitable techniques, which include but are not limited to: determining the reference cardiac parameter value based on a previously determined cardiac parameter value for the same subject for a time interval different than the time interval of interest; determining the reference cardiac parameter value based on cardiac parameter values associated with one or more averages of one or more identified populations, including in some embodiments a representative sample of the population at large; and/or the like. In particular embodiments, the reference cardiac parameter value may comprise a "baseline" estimate of the cardiac parameter of the same individual corresponding to a different time period. In some embodiments, the "baseline" time period may comprise a time period where independent observations of stress level (such as through subjective assessments from psychologist, or other means known to those skilled in the art) have determined that the individual was in a low-stress state or an otherwise known stress state.

In particular embodiments, the block 311 cardiac stress index $I_c$ is determined using a function $F_c$ of one or more of the block 304 cardiac parameters $C_i$. In one particular embodiment, the cardiac function $F_c$ comprises a function of the non-limiting exemplary form $F_c(C_i, w_i) = \text{Sum}_i\{100/[1+\exp(w_iC_i+b_i)]\}$, where: i is an index variable that spans the range of one or more of the block 304 cardiac parameters $C_i$; $\text{Sum}_i$ refers to the algebraic sum across all values of index variable; $C_i$ is the set of block 304 cardiac parameters; $w_i$ are a set of weights for each of the correspondingly indexed cardiac parameters $C_i$; and $b_i$ is a set of calibration constants. Values for the parameters $w_i$ and $b_i$ may determined using a calibration procedure which involves fitting the method 300 model to a population data set wherein each member of the population data set has an independently assessed stress value, and/or the like.

In some embodiments, the block 311 process for determining a cardiac stress index $I_c$ 311 may be based in part on one or more block 305 physical activity parameters $P_i$ in addition to the one or more block 304 cardiac parameters $C_i$. Non-limiting examples of techniques that may be used to determine a cardiac stress index $I_c$ based in part of the block 305 physical activity parameters $P_i$ include, but are non-limited to: excluding cardiac parameters $C_i$ that are associated with time intervals in which a corresponding physical activity parameter $P_i$ indicates the individual was highly active; recalculating cardiac parameters $C_i$ to exclude time periods where a physical activity parameter $P_i$ indicates the individual was highly active; adjusting a cardiac parameter $C_i$ with an adjustment factor based on an activity level indicated by a physical activity parameter $P_i$; and/or the like.

Returning now to branch 320 of method 300, block 306 involves receiving physical activity history data. As discussed above, one exemplary form of physical activity history data that could be received in block 306 is actigraphy data of the type described in connection with FIG. 2A. Techniques for actually communication the physical activity history data in block 306 to the computer implementing method 300 may be similar to those discussed above for heart beat data in block 302.

The block 306 physical activity history data may then be used in block 305 to determine one or more physical activity parameters $P_i$. In some embodiments, each physical activity parameter $P_i$ determined in block 305 comprises a numerical value that summarizes or is otherwise representative of a corresponding characteristic of an individual's gross motor activity (e.g. as represented by the block 306 physical activity history data). A physical activity parameter $P_i$ determined in block 305 may be correlated with the stress of the individual whose physical activity history data is received in block 306. In some embodiments, multiple physical activity parameters $P_i$ may be determined in block 305. In some embodiments, the block 306 physical activity history data may be separated into multiple time segments or may otherwise comprise multiple time intervals of interest and block 305 may involve the determination of one or more corresponding physical activity parameters $P_i$ for each time segment/interval.

Figure 5A:
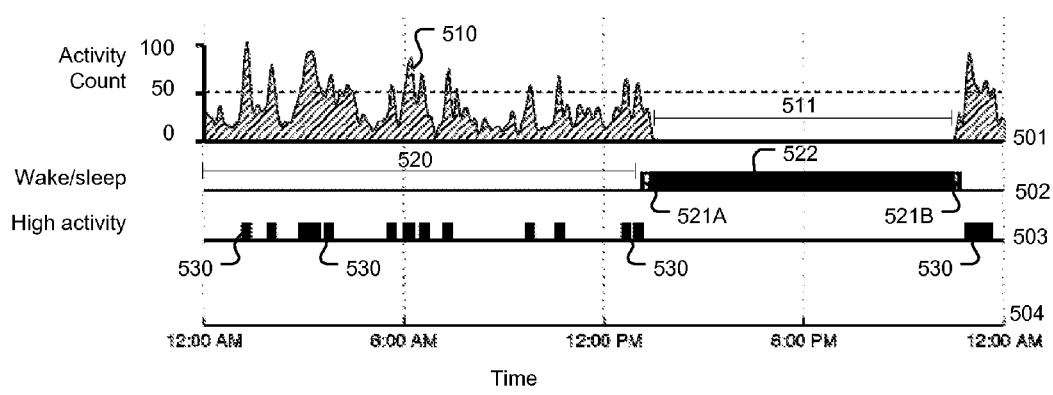
FIG. 5A shows an example of physical activity history data for an individual for a 24-hour period, with corresponding sleep history data and physical activity parameters which may be determined based on the physical activity history data in accordance with various embodiments.
Figure 5B:
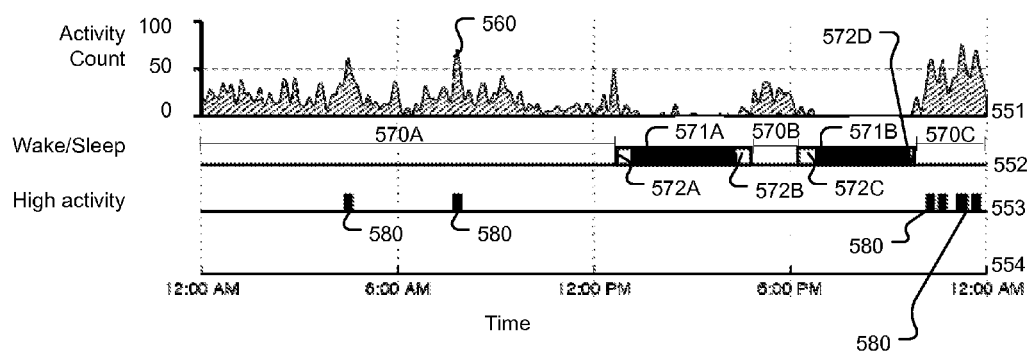
FIG. 5B shows an example of physical activity history data for the same individual for a second 24-hour period, with corresponding sleep history data and physical activity parameters which may be determined based on the physical activity history data in accordance with various embodiments.

Non-limiting examples of physical activity parameters $P_i$ which may be determined in block 305 include: total activity count in a suitable time period (e.g. a 12 or 24 hour time period), mean activity count (act_mean) in suitable time period (e.g. a 12 or 24 hour time period); and/or the like. FIG. 5A illustrates an example of block 306 physical activity history data 510 for an individual from a first 24 hour period and FIG. 5B illustrates an example of block 306 physical activity history data for the same individual from a second 24 hour period. During the first period (FIG. 5A), the individual had a higher activity level than in the second period (FIG. 5B). This higher activity level is reflected in the physical activity parameter (act mean) corresponding to the mean activity count, which is 18 for the first period (FIG. 5A) and 15 for the second period (FIG. 5B).

In some embodiments, the individual's sleep/wake state may be estimated based on the block 306 physical activity history data as one of the block 305 physical activity parameters. A variety of techniques for estimating sleep/wake state from physical activity parameters are known to those skilled in the art. In some embodiments, time segments may be classified into a sleep/wake state based on comparing activity count values for the time segment to one or more activity count thresholds (e.g. time segments with activity counts below 10 may be classified as sleep). In some embodiment heuristic rules may be combined with activity count threshold classifications, non-limiting examples of which include: classifying three or more consecutive time segments with activity counts below a low threshold value as sleep; classifying time segments as "rest in bed" if it has activity counts below a medium threshold level, and is adjacent to a segment previously classified sleep; and/or the like. Using techniques known to those skilled in the art, periods of extended minimal activity may be classified at sleep. Periods of low activity at the beginning and end of a sleep period may be classified at resting in bed. In some embodiments, a block 305 physical activity parameter $P_i$, may be determined based in part on a determined sleep state of the individual. Non-limiting examples include mean activity count during periods of wakefulness (act_wake_mean), and standard deviation of activity counts during periods of wakefulness (act_wake_std). These examples of block 305 physical activity parameters $P_i$ are shown for the physical activity history data 510, 560 of FIGS. 5A and 5B.

In some embodiments, determining the block 305 physical activity parameters $P_i$ may involve comparing activity counts to a high activity threshold. In the illustrative examples of FIGS. 5A and 5B, the high activity threshold is set at 50. In the case of physical activity history data 510 of FIG. 5A, high activity flags 530 are set for times where the activity count of physical activity history data 510 is greater than the high activity threshold. Similar high activity flags 580 are set for physical activity history data 560 of FIG. 5B. In some embodiments, a block 305 physical activity parameter $P_i$, may be determined based in part on periods of high activity. Non-limiting examples include a sum total duration of time within a specified period (e.g. 24 hours) where the high activity flags 530, 580 are set (act_time_high).

After determining one or more physical activity parameters $P_i$ in block 305, method 300 proceeds to block 309 which involves determining a physical activity stress index $I_p$ based at least in part on the one or more block 305 physical activity parameters $P_i$. In accordance with some embodiments, determining the physical activity stress index $I_p$ in block 309 may comprise transforming one or more of the values of the block 305 physical activity parameters $P_i$ using a numeric transfer function.

In particular embodiments, determining the physical activity stress index $I_p$ in block 309 may comprise using a block 305 physical activity parameter $P_i$ as a index into a look-up table in which ranges of physical activity parameter values are associated with corresponding values for the physical activity stress index $I_p$. In other embodiments, determining the physical activity stress index $I_p$ in block 309 may comprise determining a difference metric between a value of a physical activity parameter $P_i$ determined in a time interval of interest and a reference physical activity parameter value, and, optionally transforming the difference metric using a suitable transfer function. The reference physical activity parameter value may be determined using a variety of suitable techniques, which include but are not limited to: determining the reference physical activity parameter value based on a previously determined physical activity parameter value for the same subject for a time interval different than the time interval of interest; determining the reference physical activity parameter value based on physical activity parameter values associated with one or more averages of one or more identified populations, including in some embodiments a representative sample of the population at large; and/or the like. In particular embodiments, the reference physical activity parameter value may comprise a "baseline" estimate of the physical activity parameter of the same individual corresponding to a different time period. In some embodiments, the "baseline" time period may comprise a time period where independent observations of stress level (such as through subjective assessments from psychologist, or other means known to those skilled in the art) have determined that the individual was in a low-stress state or an otherwise known stress state.

In particular embodiments, the block 309 physical activity stress index $I_p$ is determined using a function $F_p$ of one or more of the block 305 physical activity parameters $P_i$. In one particular embodiment, the physical activity function $F_p$ comprises a function of the non-limiting exemplary form $F_p(P_i, w_i) = \text{Sum}_i\{100/[1+\exp(w_i P_i + b_i)]\}$, where: i is an index variable that spans the range of one or more of the block 305 physical activity parameters $P_i$; $\text{Sum}_i$ refers to the algebraic sum across all values of index variable i; $P_i$ is the set of block 305 physical activity parameters; $w_i$ are a set of weights for each of the correspondingly indexed physical activity parameters $P_i$; and $b_i$ is a set of calibration constants. Values for the parameters $w_i$ and $b_i$ may determined using a calibration procedure which involves fitting the method 300 model to a population data set wherein each member of the population data set has an independently assessed stress value, and/or the like.

Returning now to branch 330 of method 300, block 301 involves receiving sleep history data. As discussed above, one exemplary form of sleep history data that could be received in block 301 is sleep history data of the type described in connection with FIG. 2B. Techniques for actually communication the sleep history data in block 301 to the computer implementing method 300 may be similar to those discussed above for heart beat data in block 302.

The block 301 sleep history data may then be used in block 303 to determine one or more sleep parameters $S_i$. In some embodiments, each sleep parameter $S_i$ determined in block 303 comprises a numerical value that summarizes or is otherwise representative of a corresponding characteristic of an individual's sleep and wake state over the time interval of interest (e.g. as represented by the block 301 sleep history data). A sleep parameter $P_i$ determined in block 303 may be correlated with the stress of the individual whose sleep history data is received in block 301. In some embodiments multiple sleep parameters $S_i$ may be determined in block 303. In some embodiments, the block 301 sleep history data may be separated into multiple time segments or may otherwise comprise multiple time intervals of interest and block 303 may involve the determination of one or more sleep parameters $S_i$ for each time segment/interval.

Figure 6B:
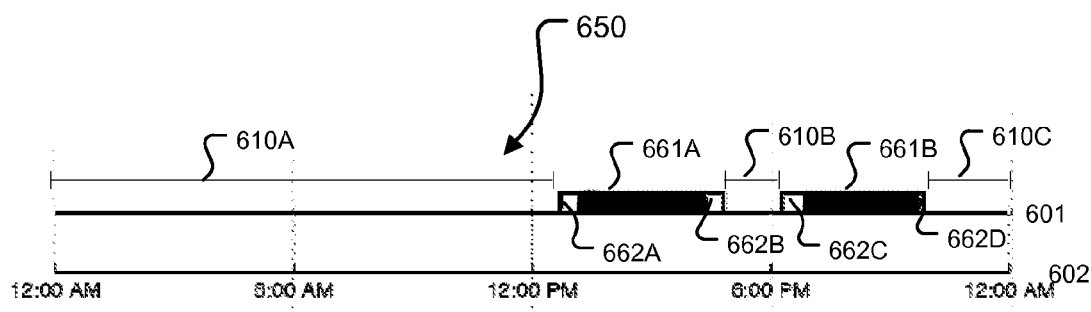
FIG. 6B shows an example of sleep history data for a 24-hour period derived from the FIG. 5B physical activity history data, with corresponding sleep parameters which may be determined based on the sleep history data in accordance with various embodiments.
Figure 6A:
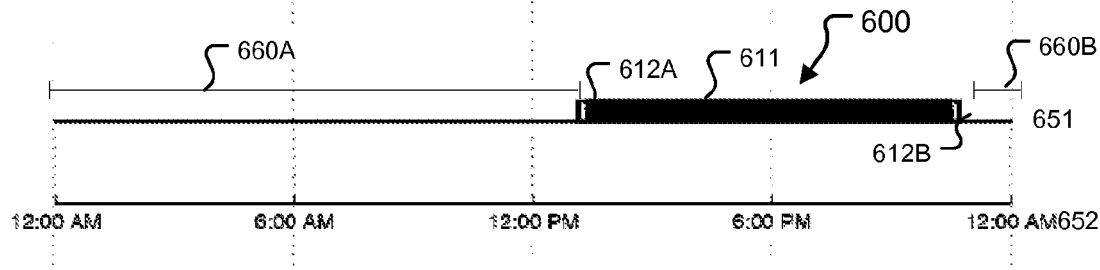
FIG. 6A shows an example of sleep history data for a 24-hour period derived from the FIG. 5A physical activity history data, with corresponding sleep parameters which may be determined based on the sleep history data in accordance with various embodiments.

Non-limiting examples of sleep parameters $S_i$ that may be determined in block 303 include: total sleep time (TST); time in bed (TIB); total wake after first sleep onset (WASO); sleep onset latency; sleep efficiency; number of awakenings; average length of awake episodes; maximum length of awake episodes; average length of sleep episodes; average activity count; standard deviation of activity count; and/or the like in suitable time period (e.g. a 12 or 24 hour time period or a time period of interest). FIG. 6A illustrates an example of block 301 sleep history data 600 for an individual from a first 24 hour period (the same 24 hour period of FIG. 5A) and FIG. 6B illustrates an example of block 301 sleep history data 650 for the same individual from a second 24 hour period (the same 24 hour period of FIG. 5B). During the first 24 hour period (FIG. 6A), the individual had a single consolidated sleep 611. During the second 24 hour period (FIG. 6B), the individual had a relatively more fragmented sleep, which resulted in two sleep periods 661A, 661B.

Each block 303 sleep parameter $S_i$ is representative of a corresponding characteristic of human sleep that may be correlated to the individual's stress level. Such characteristics of human sleep may include: sleep quality, sleep duration, sleep timing, and/or the like. Total sleep time (TST) refers to the sum of all time an individual is determined to be asleep within a given time period (e.g., 24 hours) or during an identified sleep period (e.g., a typical eight-hour period identified as an individual's typical sleep "night"). Lower TST values may be associated with higher levels of stress, since it is common for highly stressed individuals to experience reduced sleep duration and increased sleep fragmentation.

Time in bed (TIB) refers to the total amount of time an individual is determined to be in bed, whether asleep or awake, during a suitable period. Changes in TIB may be correlated to changes in levels of stress.

Total wake time after first sleep onset (WASO) refers to the total duration of time an individual is awake after it is determined that he or she has first fallen asleep after going to bed during a suitable period and before the individual has commenced a waking period of sufficient duration. Commonly there is an initial wake period after an individual goes to bed but before the individual falls asleep (see, for example, period 612A of sleep history data 600 (FIG. 6A) and periods 662A, 662C of sleep history data 650 (FIG. 6B)). WASO may be determined by disregarding this initial period of wakefulness but then summing the duration(s) of any subsequent wake periods, up to the time that the individual commences a long waking period which is determined to be such when the waking period extends for more than a long-wake threshold value. The start of the final waking period is treated as the end of a period that the individual is attempting to sleep, and the duration of that waking period is not included in the WASO. Referencing FIG. 6B, for example, the first sleep onset occurs at the beginning of period 661A. Subsequent wake periods 662B, 610B, and 662C have a total duration of 2.75 h, so if the long wake threshold was 3 h, then these periods would be included in the WASO. Waking period 610C has a duration extending past 3 h, so it would not be included in the WASO, and the final WASO value for this time interval 650 would be 2.75 h. Higher WASO values may be correlated to higher levels of stress, since stress generally increases sleep fragmentation.

Sleep onset latency is the name of the initial period of wakefulness between when the individual goes to bed and when the individual falls asleep (see, for example, period 612A of sleep history data 600 (FIG. 6A) and periods 662A, 662C of sleep history data 650 (FIG. 6B)). Higher sleep onset latency values may be correlated to higher levels of stress.

Sleep efficiency refers to the ratio of total sleep time to time in bed (i.e., TST/TIB). Lower sleep efficiency values may be correlated to higher levels of stress, since stress generally increases sleep fragmentation.

The number of awakenings refers to how many times during an identified sleep interval or other suitable period it is determined that the individual wakes up. A higher number of awakenings may be correlated to higher levels of stress, since stress generally increases sleep fragmentation.

Average length of awake episodes refers to the average duration of the episodes in which the individual is awake during an identified sleep period or other suitable period (see, for example, period 610B in sleep history data 650 (FIG. 6B). Longer average length of awake episodes may be correlated to higher levels of stress.

Maximum length of sleep episodes refers to the longest duration of sleep during a suitable period. Shorter maximum length of sleep episodes may be correlated to higher levels of stress.

After determining one or more sleep parameters $S_i$ in block 303, method 300 proceeds to block 307 which involves determining a sleep stress index $I_s$ based at least in part on the one or more block 303 sleep parameters $S_i$. In accordance with some embodiments, determining the sleep stress index $I_s$ in block 307 may comprise transforming one or more of the values of the block 303 sleep parameters $S_i$ using a numeric transfer function.

In particular embodiments, determining the sleep stress index $I_s$ in block 307 may comprise using a block 303 sleep parameter $S_i$ as an index into a look-up table in which ranges of sleep parameter values are associated with corresponding values for the sleep stress index $I_s$. In other embodiments, determining the sleep stress index $I_s$ in block 307 may comprise determining a difference metric between a value of a sleep parameter $S_i$ determined in a time interval of interest and a reference sleep parameter value, and, optionally, transforming the difference metric using a suitable transfer function. The reference sleep parameter value may be determined using a variety of suitable techniques, which include but are not limited to: determining the reference sleep parameter value based on a previously determined sleep parameter value for the same subject for a time interval different than the time interval of interest; determining the reference sleep parameter value based on sleep parameter values associated with one or more averages of one or more identified populations, including in some embodiments a representative sample of the population at large; and/or the like. In particular embodiments, the reference sleep parameter value may comprise a "baseline" estimate of the sleep parameter of the same individual corresponding to a time interval where independent observations of stress level (such as through subjective assessments from psychologist, or other means known to those skilled in the art) have determined that the individual was in a low-stress state or an otherwise known stress state.

In particular embodiments, the block 307 sleep stress index $I_s$ is determined using a function $F_s$ of one or more of the block 303 sleep parameters $S_i$. In one particular embodiment, the sleep function $F_s$ comprises a function of the non-limiting exemplary form $F_s(S_i, w_i) = \text{Sum}_i\{100/[1+\exp(w_i S_i + b_i)]\}$, where: i is an index variable that spans the range of one or more of the block 303 sleep parameters $S_i$; $\text{Sum}_i$ refers to the algebraic sum across all values of index variable i; $S_i$ is the set of block 303 sleep parameters; $w_i$ are a set of weights for each of the correspondingly indexed sleep parameters $S_i$, and $b_i$ is a set of calibration constants. Values for the parameters $w_i$ and $b_i$ may determined using a calibration procedure which involves fitting the method 300 model to a population data set wherein each member of the population data set has an independently assessed stress value, and/or the like.

Method 300 then proceeds to block 306 which involves determining a composite stress index I based at least in part on the block 304 cardiac stress index $I_c$ and one or both of: the block 309 physical-activity stress index $I_p$ and the block 303 sleep stress index $I_s$. The block 306 composite stress index I may be determined by techniques that include, but are not limited to: determining the average of the input indices ($I_c$ and one of both of $I_s$ and $I_p$), values; determining the maximum of the input indices ($I_c$ and one of both of $I_s$ and $I_p$); determining a linear combination of the input indices ($I_c$ and one of both of $I_s$ and $I_p$); referencing a look-up table that associates values of the input indices ($I_c$ and one of both of $I_s$ and $I_p$) with composite stress index/values and/or the like.

Figure 4:
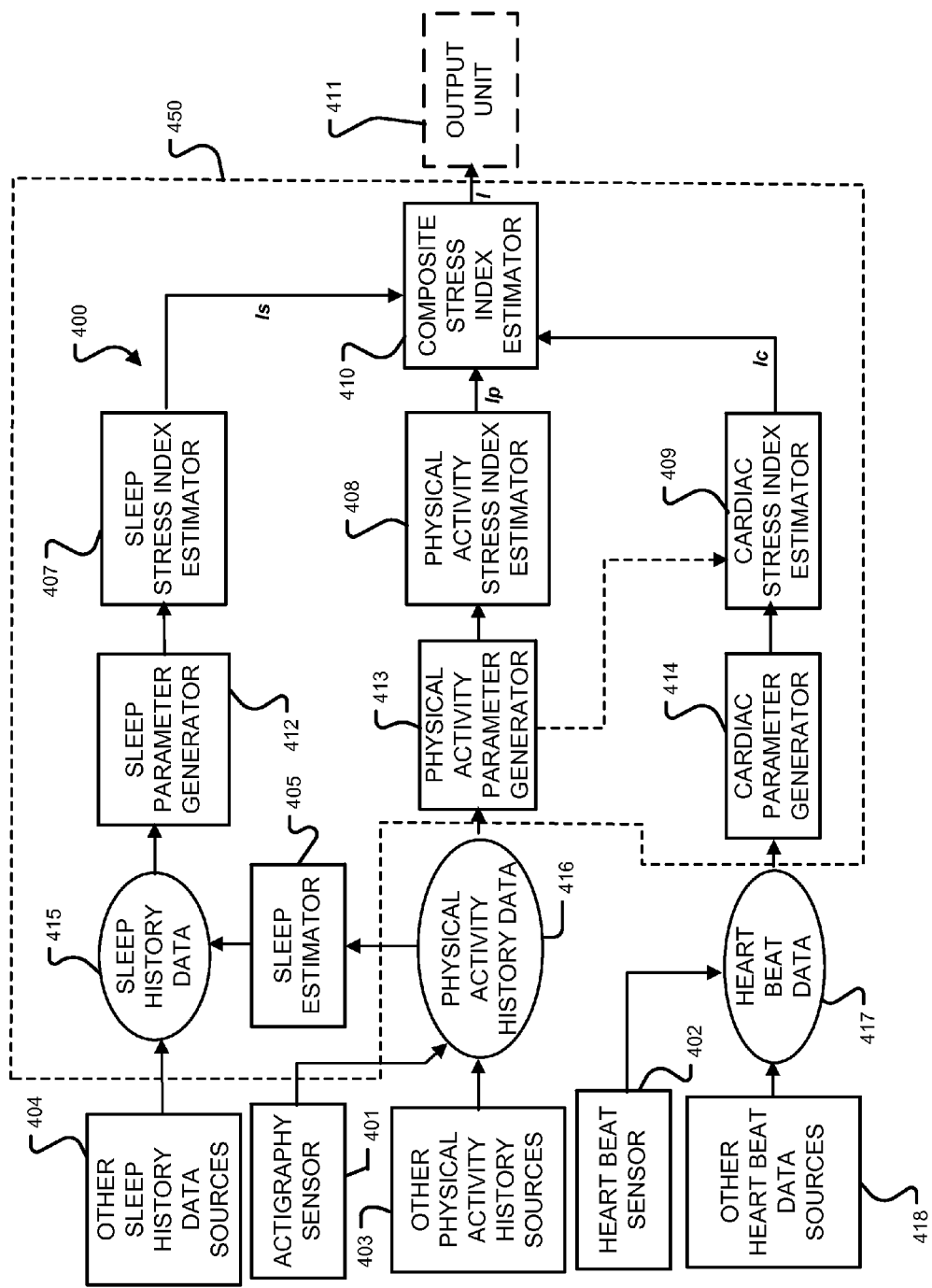
FIG. 4 is a block diagram illustrating a system for determining a composite stress index according to a particular embodiment.

FIG. 4 provides a block diagram of a system 400 for determining a composite stress index I in accordance with a particular embodiment. System 400 of the illustrated embodiment, which is capable of executing method 300 (FIG. 3), includes or has access to an actigraphy sensor 401 and a heart beat sensor 402.

Actigraphy sensor 401 may be of the type described above. Actigraphy sensor may comprise an accelerometer sensor housed inside a device which may be affixed to a location on an individual's body or a garment worn by the individual. Gross motor activity of the individual to which actigraphy sensor 401 is attached may result in translational movement of actigraphy sensor 401, which is detected by the accelerometer. Non-limiting examples of gross motor activity include arm movements, walking, running, and/or the like. As discussed above, in some embodiments, actigraphy sensor 401 stores an activity count in its internal memory or in other memory to which it has access. The output of actigraphy sensor 401 provides at least a part of physical activity history data 416. Actigraphy sensor 401 may comprise a memory storage component (not shown) for storing measured physical activity values, and communication components (not shown) for communicating physical activity history data 416 to other components of system 400.

Heart beat sensor 402 may comprise a sensor that detects one or more aspects of cardiac activity. In particular embodiments, heart beat sensor 402 may be one of an ECG holter monitors, a blood pressure sensors, a photoplethysmography sensor (PPG) or "pulse oximeter" and or the like. The output of heart beat sensor 402 provides at least a part of heart beat data 417. Heart beat sensor 402 may comprise a memory storage component (not shown) for storing measured heart beat data, and communication components for communicating heart beat data 417 to other components of system 400.

In some embodiments actigraphy sensor 401 and heart beat sensor 402 may comprise a single wrist-worn unit. In other embodiments, actigraphy sensor 401 may comprise a wrist-worn device, and heart beat sensor 402 may comprise a chest-worn device communicably connected to wrist-worn actigraphy sensor 401 through any of several communication modes as are known in the art (hard wired, RF, IF, USB, Bluetooth®, and/or the like).

System 400 may also optionally receive physical activity history data 416 from other sources 403. In some embodiments other sources 403 of physical activity history data may comprise: a software module producing physical activity history data as an output (e.g. software that interacts with an individual to interrogate the individual about their physical activity history); a database (e.g. containing historical physical activity history data, baseline physical activity history data, population average physical activity history data and/or the like); an activity sensor of a different variety than an actigraphy sensor 401 (e.g. another type of motion sensor); a communication component that receives physical activity history data from some other source; a user input device (e.g. which may allow individual to enter physical activity history data kept in an activity log); and/or the like.

System 400 may also optionally receive heart beat data 417 from other sources 418. In some embodiments other sources 418 of heart beat data may comprise: a software module producing heart beat data as an output (e.g. software that interacts with an individual to interrogate the individual about their heart beat data); a database (e.g. containing historical heart beat data, baseline heart beat data, population average heart beat data and/or the like); another heart beat sensor which may be of a different type than heart beat sensor 402; a communication component that receives heart beat data from some other source; and/or the like.

System 400 comprises a processor 450 shown in dashed outline in FIG. 4. Processor 450 may comprise a part of a suitably configured computer system (not shown) or may be part of an embedded system. Processor 450 may comprise more than one individual data processor which may be centrally located and/or distributed. Processor 450 may comprise internal memory (not shown) and/or have access to external memory (not shown). Processor 450 may be programmed with, or otherwise have access to, software (not shown) which may cause processor 450 to implement at least portions of the methods described herein. Suitable interfacing hardware and/or software (not shown) may be provided between processor 450 and the other components of system 400. By way of non-limiting example, such interfacing hardware and/or software may include: signal conditioning components, analog-to-digital converters, networking and/or other communications components, buffers, memory and/or the like.

In the illustrated embodiment, controller 450 comprises an optional sleep estimator 405. Sleep estimator 405 processes physical activity history data 416 to generate sleep history data 415. Using techniques known to those skilled in the art, periods of extended minimal activity may be classified at sleep (see, for example, sleep periods 522 (FIG. 5A) and 571A, 571B (FIG. 5B)). Periods of low activity at the beginning and end of a sleep period may be classified at resting in bed (see, for example, periods 521A, 521B (FIG. 5A) and 572A, 572B, 572C, 572D (FIG. 5B)). Sleep estimator 405 may incorporate a mathematical model of sleep propensity and base the determination of sleep periods at least in part on predicted sleep propensity. Probability-based techniques and/or heuristic algorithms may incorporate an individual's sleep propensity, such that periods in which an individual's predicted sleep propensity is high will have a higher likelihood of being classified as sleep periods, and periods with a low sleep propensity will have a higher likelihood of being classified as periods of wakefulness. Sleep estimator 405 may be implemented as a software module. In the illustrated embodiment, sleep estimator 405 is executed by system processor 450. In other embodiments, sleep estimator 405 may be executed by a microprocessor or computer unit associated with actigraphy sensor 401 or by its own dedicator processor.

In still other embodiments, sleep estimator 405 is not required as sleep history data may be obtained from other source(s) 404, rather than being derived from physical activity history data 416. In some embodiments, other sleep history data sources 404 may comprise: a software module producing sleep history data as an output (e.g. software that interacts with an individual to interrogate the individual about their sleep history); a database (e.g. containing historical sleep history data, baseline sleep history data, population average sleep history data and/or the like); a communication component that receives sleep history data from some other source; a user input device (e.g. which may allow individual to enter sleep history data kept in an activity log); and/or the like.

Processor 450 may also be configured to implement one or more of: sleep parameter generator 412, cardiac parameter generator 414, and physical activity parameter generator 413. Sleep parameter generator 412 receives sleep history data 415 and determines one or more sleep parameters $S_i$ of the type discussed above—e.g. sleep parameter generator 412 may perform block 303 of method 300 (FIG. 3). Cardiac parameter generator 414 receives heart beat data 417 and determines one or more cardiac parameters $C_i$ of the type discussed above—e.g. cardiac parameter generator 414 may perform block 304 of method 300 (FIG. 3). Physical activity parameter generator 413 receives physical activity history data 416 and determines one or more physical activity parameters $P_i$ of the type discussed above—e.g. physical activity parameter generator 413 may perform block 305 of method 300 (FIG. 3). In the illustrated embodiment, parameter generators 412, 413, 414 are all implemented by processor 450. In other embodiments, one or more of parameter generators 412, 413, 414 may be implemented by different processors.

Processor 450 may also be configured to implement: sleep stress index estimator 407, physical activity stress index estimator 408, and cardiac stress index estimator 409, which are respectively used to determine the sleep stress index $I_s$ (based on the one or more sleep parameters $S_i$) physical-activity stress index $I_p$ (based on the one or more physical activity parameters $P_i$), and cardiac stress index $I_c$ (based on the one or more cardiac parameters $C_i$). For example, sleep stress index estimator 407, physical activity stress index estimator 408, and cardiac stress index estimator 409 may respectively perform blocks 307, 309 and 311 of method 300 (FIG. 3). In the illustrated embodiment, stress index generators 407, 408, 409 are all implemented by processor 450. In other embodiments, one or more of stress index generators 407, 408, 409 may be implemented by different processors.

Processor 450 of the illustrated embodiment is also configured to implement composite stress index estimator 410. Composite stress index estimator 410 determines composite stress index I based on cardiac stress index $I_c$ and one or both of physical activity stress index $I_p$ and sleep stress index $I_s$—e.g. composite stress index estimator 410 may perform block 306 of method 300 (FIG. 3).

System 400 may also comprise an optional output unit 411, which may output to a user or other system the composite stress index I determined by composite stress index estimator 410. Output unit 411 may comprise any suitable device for outputting data, which by way of non-limiting example may include a screen, a printer, a network interface, a telecommunications link, an audible device, and/or the like.

Technological and commercial applications for stress quantification and management can be found in the space exploration, military, manufacturing, heavy industrial, transportation, law-enforcement, and emergency-response industries, among others. Critical applications of the presently disclosed systems and methods can be found for example in the work scheduling and stress countermeasure management systems for space flight crews. Additional applications can be found in monitoring the readjustment to civilian life of returning active military personnel, who often have a variety of undiagnosed and untreated stress-related adjustment difficulties, including but not limited to PTSD and physiological difficulties with stimulant withdrawal akin to addiction recovery. Ordinary civilian medicine applications also abound, including the diagnosis and treatment monitoring for PTSD. Several embodiments of the presently disclosed system and method are capable of stress monitoring for a plurality of testing subjects, and therefore workplace-management and scientific-research applications can be easily fashioned therefrom.

Certain implementations of the invention comprise computer processors which execute software instructions which cause the processors to perform a method of the invention. For example, one or more processors in an actigraphy system may implement data processing steps in the methods described herein by executing software instructions retrieved from a program memory accessible to the processors. The invention may also be provided in the form of a program product. The program product may comprise any medium which carries a set of computer-readable instructions which, when executed by a data processor, cause the data processor to execute a method of the invention. Program products according to the invention may be in any of a wide variety of forms. The program product may comprise, for example, physical media such as magnetic data storage media including floppy diskettes, hard disk drives, optical data storage media including CD ROMs, DVDs, electronic data storage media including ROMs, flash RAM, or the like. The instructions may be present on the program product in encrypted and/or compressed formats.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e. that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:
- actigraphy sensor 401 may comprise other functionality that may include but is not limited to: a clock, timer, and alarm;
- while physical activity history data is collected in the preferred embodiment of actigraphy sensor 401 described above, other types of suitable physiological data may be collected in addition to or as an alternative to physical activity history data. Such physiological data measurement systems may collect more than one type of physiological data.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for determining a composite stress index for an individual using a computer, the method comprising:
    providing heart beat data at the computer the heart beat data representative of the individual's cardiac activity during the time interval of interest;
    determining one or more cardiac parameters based on the heart beat data, each cardiac parameter associated with a corresponding characteristic of the individual's cardiac activity during the time interval of interest;
    determining a cardiac stress index for the individual based on the one or more cardiac parameters;
    providing sleep history data at a computer, the sleep history data comprising one or more sleep onset times and one or more awakening times for an individual during a time interval of interest;
    determining one or more sleep parameters based on the sleep history data, each sleep parameter associated with a corresponding characteristic of the individual's sleep during the time interval of interest;
    determining a sleep stress index for the individual based on the one or more sleep parameters; and
    determining a composite stress index based at least in part on one or more of the cardiac stress index and the sleep stress index.

2. A method according to claim 1 wherein the one or more cardiac parameters comprise one or more of:
    an average heart rate of the heart beat data over the time interval of interest;
    a standard deviation of R-R intervals in the heart beat data over the time interval of interest;
    a root mean squared difference of successive R peaks in the heart beat data over the time interval of interest;
    a number of pairs of successive R-R intervals in the heart beat data over the time interval of interest that differ by more than a threshold time
    a ratio of a number of pairs of successive R-R intervals in the heart beat data over the time interval of interest that differ by more than a threshold time divided by a total number of R-R intervals in the heart beat data over the time interval of interest; and
    a ratio of a high-frequency power to a low frequency power within a power spectral density of an R-R interval time series constructed from the heart beat data over the time interval of interest.

3. A method according to claim 2 wherein determining the composite stress index based at least in part on both the sleep history data and the heart beat data comprises:
    determining one or more sleep parameters based on the sleep history data, each sleep parameter associated with a corresponding characteristic of the individual's sleep during the time interval of interest;
    determining a single-valued sleep stress index for the individual based on the one or more sleep parameters; and
    determining the composite stress index based at least in part on the sleep stress index;
    wherein the one or more sleep parameters comprise one or more of:
    a total wake time after first sleep onset parameter indicative of a total time that the individual is awake in bed, after a first occurrence of falling asleep, during the time interval of interest;
    a sleep onset latency parameter indicative of a total time that the individual is awake in bed, before first falling asleep, during the time interval of interest; and
    a number of awakenings parameter indicative of a total number of times the individual awakens from sleep during the time interval of interest.

4. A method according to claim 2 wherein determining the composite stress index based at least in part on both the sleep history data and the heart beat data comprises:
    determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index; wherein the one or more sleep parameters comprise a sleep efficiency parameter indicative of a ratio of a total time asleep while in bed to a total time in bed during the time interval of interest.

5. A method according to claim 2 wherein determining the composite stress index based at least in part on both the sleep history data and the heart beat data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise one or more of:

an average length of awake episodes parameter indicative of an average duration the individual is awake during each wake episode during the time interval of interest; and an average length of sleep episodes parameter indicative of an average duration the individual is asleep during each sleep episode during the time interval of interest.

6. A method according to claim 2 comprising:

providing physical activity history data at the computer, the physical activity history data representative of gross motor activity of the individual during the time interval of interest; and wherein determining the quantitative composite stress index with the computer based at least in part on both the sleep history data and the heart beat data comprises determining the composite stress index with the computer based at least in part on the sleep history data, the heart beat data and the physical activity history data.

7. A method according to claim 6 wherein determining the composite stress index based at least in part on the sleep history data, the heart beat data and the physical activity history data comprises:

determining one or more physical activity parameters based on the physical activity history data, each physical activity parameter associated with a corresponding characteristic of the individual's physical activity during the time period of interest;

determining a single-valued physical activity stress index for the individual based on the one or more physical activity parameters; and determining the composite stress index based at least in part on the physical activity stress index;

wherein the one or more physical activity parameters comprise one or more of:

a total activity count for the activity history data over the time interval of interest indicative of overall physical movement during the time interval of interest;

an average activity count for the activity history data indicative of typical physical movement during the time interval of interest;

an average activity rate for the activity history data during the time interval of interest indicative of a typical rate of physical movement during the time interval of interest; and a duration of time that an activity count of the activity history data is above a high activity count threshold over the time interval of interest indicative of a duration of high physical movement.

8. A method according to claim 7 wherein determining the composite stress index based at least in part on both the sleep history data and the heart beat data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise one or more of:

a total sleep time parameter indicative of a total time that the individual was asleep during the time interval of interest;

a time in bed parameter indicative of a total time that the individual was in bed during the time interval of interest;

a total wake time after first sleep onset parameter indicative of a total time that the individual is awake in bed, after a first occurrence of falling asleep, during the time interval of interest;

a sleep onset latency parameter indicative of a total time that the individual is awake in bed, before first falling asleep, during the time interval of interest;

a number of awakenings parameter indicative of a total number of times the individual awakens from sleep during the time interval of interest;

a sleep efficiency parameter indicative of a ratio of a total time asleep while in bed to a total time in bed during the time interval of interest;

an average length of awake episodes parameter indicative of an average duration the individual is awake during each wake episode during the time interval of interest; and an average length of sleep episodes parameter indicative of an average duration the individual is asleep during each sleep episode during the time interval of interest.

9. A method according to claim 1 wherein the one or more sleep parameters comprise one or more of:

a total sleep time parameter indicative of a total time that the individual was asleep during the time interval of interest; and a time in bed parameter indicative of a total time that the individual was in bed during the time interval of interest.

10. A method according to claim 1 comprising:

providing physical activity history data at the computer, the physical activity history data representative of gross motor activity of the individual during the time interval of interest; and wherein determining the quantitative composite stress index with the computer based at least in part on both the sleep history data and the heart beat data comprises determining the composite stress index with the computer based at least in part on the sleep history data, the heart beat data and the physical activity history data.

11. A method according to claim 10 wherein determining the composite stress index based at least in part on the sleep history data, the heart beat data and the physical activity history data comprises:

determining one or more physical activity parameters based on the physical activity history data, each physical activity parameter associated with a corresponding characteristic of the individual's physical activity during the time period of interest;

determining a single-valued physical activity stress index for the individual based on the one or more physical activity parameters; and determining the composite stress index based at least in part on the physical activity stress index;

wherein the one or more physical activity parameters comprise one or more of:

a total activity count for the activity history data over the time interval of interest indicative of overall physical movement during the time interval of interest;

an average activity count for the activity history data indicative of typical physical movement during the time interval of interest;

an average activity rate for the activity history data during the time interval of interest indicative of a typical rate of physical movement during the time interval of interest; and a duration of time that an activity count of the activity history data is above a high activity count threshold over the time interval of interest indicative of a duration of high physical movement.

12. A method according to claim 11 wherein determining the composite stress index based at least in part on both the sleep history data and the heart beat data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise one or more of:

a total sleep time parameter indicative of a total time that the individual was asleep during the time interval of interest; and a time in bed parameter indicative of a total time that the individual was in bed during the time interval of interest.

13. A method according to claim 11 wherein determining the composite stress index based at least in part on both the sleep history data and the heart beat data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise one or more of:

a total wake time after first sleep onset parameter indicative of a total time that the individual is awake in bed, after a first occurrence of falling asleep, during the time interval of interest;

a sleep onset latency parameter indicative of a total time that the individual is awake in bed, before first falling asleep, during the time interval of interest; and a number of awakenings parameter indicative of a total number of times the individual awakens from sleep during the time interval of interest.

14. A method according to claim 11 wherein determining the composite stress index based at least in part on both the sleep history data and the heart beat data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise a sleep efficiency parameter indicative of a ratio of a total time asleep while in bed to a total time in bed during the time interval of interest.

15. A method according to claim 11 wherein determining the composite stress index based at least in part on both the sleep history data and the heart beat data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise one or more of:

an average length of awake episodes parameter indicative of an average duration the individual is awake during each wake episode during the time interval of interest; and an average length of sleep episodes parameter indicative of an average duration the individual is asleep during each sleep episode during the time interval of interest.

16. A method according to claim 10 wherein the physical activity data comprises data representative of the gross motor activity of the individual during a second time interval and wherein determining the composite stress index based at least in part on the sleep history data, the heart beat data and the physical activity history data comprises:

determining a first physical activity parameter associated with a corresponding characteristic of the individual's physical activity based on the physical activity history data during the time period of interest;

determining a second physical activity parameter associated with the corresponding characteristic of the individual's physical activity based on the physical activity history data during the second time period;

comparing the first physical activity parameter to the second physical activity parameter to determine a difference metric therebetween; and determining the composite stress index based at least in part on the difference metric.

17. A method according to claim 10 wherein providing physical activity history data comprises providing actigraphy data measured by an actigraphy sensor and wherein providing sleep history data comprises deriving the sleep history data from the actigraphy data.

18. A method according to claim 1 wherein determining the composite stress index based at least in part on both the sleep history data and the heart beat data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and
determining the composite stress index based at least in part on the sleep stress index;
wherein the one or more sleep parameters comprise one or more of:
a total sleep time parameter indicative of a total time that the individual was asleep during the time interval of interest; and
a time in bed parameter indicative of a total time that the individual was in bed during the time interval of interest.

19. A method according to claim 1 wherein determining the composite stress index based at least in part on both the sleep history data and the heart beat data comprises:
determining one or more sleep parameters based on the sleep history data, each sleep parameter associated with a corresponding characteristic of the individual's sleep during the time interval of interest;
determining a single-valued sleep stress index for the individual based on the one or more sleep parameters; and
determining the composite stress index based at least in part on the sleep stress index;
wherein the one or more sleep parameters comprise one or more of:
a total wake time after first sleep onset parameter indicative of a total time that the individual is awake in bed, after a first occurrence of falling asleep, during the time interval of interest;
a sleep onset latency parameter indicative of a total time that the individual is awake in bed, before first falling asleep, during the time interval of interest; and
a number of awakenings parameter indicative of a total number of times the individual awakens from sleep during the time interval of interest.

20. A method according to claim 1 wherein determining the composite stress index based at least in part on both the sleep history data and the heart beat data comprises:
determining one or more sleep parameters based on the sleep history data, each sleep parameter associated with a corresponding characteristic of the individual's sleep during the time interval of interest;
determining a single-valued sleep stress index for the individual based on the one or more sleep parameters; and
determining the composite stress index based at least in part on the sleep stress index;
wherein the one or more sleep parameters comprise a sleep efficiency parameter indicative of a ratio of a total time asleep while in bed to a total time in bed during the time interval of interest.

21. A method according to claim 1 wherein determining the composite stress index based at least in part on both the sleep history data and the heart beat data comprises:
determining one or more sleep parameters based on the sleep history data, each sleep parameter associated with a corresponding characteristic of the individual's sleep during the time interval of interest;
determining a single-valued sleep stress index for the individual based on the one or more sleep parameters; and
determining the composite stress index based at least in part on the sleep stress index;
wherein the one or more sleep parameters comprise one or more of:
an average length of awake episodes parameter indicative of an average duration the individual is awake during each wake episode during the time interval of interest; and
an average length of sleep episodes parameter indicative of an average duration the individual is asleep during each sleep episode during the time interval of interest.

22. A method according to claim 1 wherein the sleep history data comprises one or more sleep onset times and one or more awakening times for the individual during a second time interval and wherein determining the composite stress index based at least in part on both the sleep history data and the heart beat data comprises:
determining a first sleep parameter associated with a corresponding characteristic of the individual's sleep based on the sleep history data during the time interval of interest;
determining a second sleep parameter associated with the corresponding characteristic of the individual's sleep based on the sleep history data during the second time interval;
comparing the first sleep parameter to the second sleep parameter to determine a difference metric therebetween; and determining the composite stress index based at least in part on the difference metric.

23. A method according to claim 1 wherein the heart beat data comprises data representative of the individual's cardiac activity during a second time interval and wherein determining the composite stress index based at least in part on both the sleep history data and the heart beat data comprises:
determining a first cardiac parameter associated with a corresponding characteristic of the individual's cardiac activity based on the heart beat data during the time interval of interest;
determining a second cardiac parameter associated with the corresponding characteristic of the individual's cardiac activity based on the heart beat data during the second time interval;
comparing the first cardiac parameter to the second cardiac parameter to determine a difference metric therebetween; and
determining the composite stress index based at least in part on the difference metric.

24. A method according to claim 1 providing sleep history data comprises one or more of:
receiving a sleep log comprising the sleep history data;
receiving the sleep history data from a database;
receiving the sleep history data by interactively requesting the individual to provide the details of the sleep history data.

25. A method according to claim 1 wherein determining the composite stress index based at least in part on both the sleep history data and the heart beat data comprises:
determining one or more sleep parameters based on the sleep history data, each sleep parameter associated with a corresponding characteristic of the individual's sleep during the time interval of interest;
determining a single-valued sleep stress index for the individual based on the one or more sleep parameters; and
determining the composite stress index based at least in part on the sleep stress index;
wherein $S_i$, represents the one or more sleep parameters, and wherein determining the single-valued sleep stress index comprises evaluating a function of the form: $I_s = \mathrm{Sum}_i[N/(1+\exp(w_i S_i + b_i))]$, where $I_s$ represents the sleep stress index, $w_i$, represents a set of weights, $b_i$ represents a set of constants, and N represents a scaling factor.

26. A method according to claim 1 wherein determining the composite stress index based at least in part on both the sleep history data and the heart beat data comprises:

determining a first sleep parameter based on the sleep history data, the first sleep parameter associated with a corresponding characteristic of the individual's sleep during the time interval of interest;

providing a population average sleep parameter associated with the corresponding characteristic of a sleep history of the population;

comparing the first sleep parameter to the population average sleep parameter to determine a difference metric there between; and determining the composite stress index based at least in part on the difference metric.

27. A method according to claim 1 wherein determining the composite stress index based at least in part on both the sleep history data and the heart beat data comprises:

determining a first cardiac parameter based on the heart beat data, the first cardiac parameter associated with a corresponding characteristic of the individual's cardiac activity during the time interval of interest;

providing a population average cardiac parameter associated with the corresponding characteristic of cardiac activity of the population;

comparing the first cardiac parameter to the population average cardiac parameter to determine a difference metric therebetween; and determining the composite stress index based at least in part on the difference metric.

28. A method for determining a composite stress index for an individual using a computer, the method comprising:

receiving heart beat data at the computer, the heart beat data representative of the individual's cardiac activity during the time interval of interest;

determining one or more cardiac parameters based on the heart beat data, each cardiac parameter associated with a corresponding characteristic of the individual's cardiac activity during the time interval of interest;

determining cardiac stress index for the individual based on the one or more cardiac parameters;

receiving physical activity history data at a computer, the physical activity history data representative of gross motor activity of the individual during a time interval of interest;

determining one or more physical activity parameters based on the physical activity history data, each physical activity parameter associated with a corresponding characteristic of the individual's physical activity during the time period of;

determining a physical activity stress index for the individual based on the one or more physical activity parameters; and determining the composite stress index based at least in part on one or more of the cardiac stress index and the physical activity stress index, the composite stress index representative of a general physiological stress of the individual during the time interval of interest.

29. A method according to claim 28 wherein the one or more cardiac parameters comprise one or more of:

an average heart rate of the heart beat data over the time interval of interest;

a standard deviation of R-R intervals in the heart beat data over the time interval of interest;

a root mean squared difference of successive R peaks in the heart beat data over the time interval of interest;

a number of pairs of successive R-R intervals in the heart beat data over the time interval of interest that differ by more than a threshold time a ratio of a number of pairs of successive R-R intervals in the heart beat data over the time interval of interest that differ by more than a threshold time divided by a total number of R-R intervals in the heart beat data over the time interval of interest; and a ratio of a high-frequency power to a low-frequency power within a power spectral density of an R-R interval time series constructed from the heart beat data over the time interval of interest.

30. A method according to claim 29 comprising:

providing sleep history data at the computer, the sleep history data comprising one or more sleep onset times and one or more awakening times for an individual during a time interval of interest;

wherein determining the quantitative composite stress index with the computer based at least in part on both the activity history data and the heart beat data comprises determining the composite stress index with the computer based at least in part on the sleep history data, the heart beat data and the physical activity history data;

wherein determining the composite stress index based at least in part on the sleep history data, the heart beat data and the physical activity history data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index; and wherein the one or more sleep parameters comprise one or more of:

a total sleep time parameter indicative of a total time that the individual was asleep during the time interval of interest;

a time in bed parameter indicative of a total time that the individual was in bed during the time interval of interest;

a total wake time after first sleep onset parameter indicative of a total time that the individual is awake in bed, after a first occurrence of falling asleep, during the time interval of interest;

a sleep onset latency parameter indicative of a total time that the individual is awake in bed, before first falling asleep, during the time interval of interest;

a number of awakenings parameter indicative of a total number of times the individual awakens from sleep during the time interval of interest;

a sleep efficiency parameter indicative of a ratio of a total time asleep while in bed to a total time in bed during the time interval of interest;

an average length of awake episodes parameter indicative of an average duration the individual is awake during each wake episode during the time interval of interest; and an average length of sleep episodes parameter indicative of an average duration the individual is asleep during each sleep episode during the time interval of interest.

31. A method according to claim 28 interest wherein the one or more physical activity parameters comprise one or more of:

a total activity count for the activity history data over the time interval of interest indicative of overall physical movement during the time interval of interest;

an average activity count for the activity history data indicative of typical physical movement during the time interval of interest;

an average activity rate for the activity history data during the time interval of interest indicative of a typical rate of physical movement during the time interval of interest; and a duration of time that an activity count of the activity history data is above a high activity count threshold over the time interval of interest indicative of a duration of high physical movement.

32. A method according to claim 28 wherein determining the composite stress index based at least in part on the physical activity history data and the heart beat data comprises:

determining one or more physical activity parameters based on the physical activity history data, each physical activity parameter associated with a corresponding characteristic of the individual's physical activity during the time period of interest;

determining a single-valued physical activity stress index for the individual based on the one or more physical activity parameters; and determining the composite stress index based at least in part on the physical activity stress index;

wherein the one or more physical activity parameters comprise one or more of:

a total activity count for the activity history data over the time interval of interest indicative of overall physical movement during the time interval of interest;

an average activity count for the activity history data indicative of typical physical movement during the time interval of interest;

an average activity rate for the activity history data during the time interval of interest indicative of a typical rate of physical movement during the time interval of interest; and a duration of time that an activity count of the activity history data is above a high activity count threshold over the time interval of interest indicative of a duration of high physical movement.

33. A method according to claim 32 comprising:

providing sleep history data at the computer, the sleep history data comprising one or more sleep onset times and one or more awakening times for an individual during a time interval of interest;

wherein determining the quantitative composite stress index with the computer based at least in part on both the activity history data and the heart beat data comprises determining the composite stress index with the computer based at least in part on the sleep history data, the heart beat data and the physical activity history data;

wherein determining the composite stress index based at least in part on the sleep history data, the heart beat data and the physical activity history data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index; and wherein the one or more sleep parameters comprise one or more of:

a total sleep time parameter indicative of a total time that the individual was asleep during the time interval of interest;

a time in bed parameter indicative of a total time that the individual was in bed during the time interval of interest;

a total wake time after first sleep onset parameter indicative of a total time that the individual is awake in bed, after a first occurrence of falling asleep, during the time interval of interest;

a sleep onset latency parameter indicative of a total time that the individual is awake in bed, before first falling asleep, during the time interval of interest;

a number of awakenings parameter indicative of a total number of times the individual awakens from sleep during the time interval of interest; a sleep efficiency parameter indicative of a ratio of a total time asleep while in bed to a total time in bed during the time interval of interest;

an average length of awake episodes parameter indicative of an average duration the individual is awake during each wake episode during the time interval of interest; and an average length of sleep episodes parameter indicative of an average duration the individual is asleep during each sleep episode during the time interval of interest.

34. A method according to claim 28 comprising:

providing sleep history data at the computer, the sleep history data comprising one or more sleep onset times and one or more awakening times for an individual during a time interval of interest;

wherein determining the quantitative composite stress index with the computer based at least in part on both the activity history data and the heart beat data comprises determining the composite stress index with the computer based at least in part on the sleep history data, the heart beat data and the physical activity history data.

35. A method according to claim 34 wherein determining the composite stress index based at least in part on the sleep history data, the heart beat data and the physical activity history data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise one or more of:

a total sleep time parameter indicative of a total time that the individual was asleep during the time interval of interest; and a time in bed parameter indicative of a total time that the individual was in bed during the time interval of interest.

36. A method according to claim 34 wherein determining the composite stress index based at least in part on the sleep history data, the heart beat data and the physical activity history data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index;

wherein the one or more sleep parameters comprise one or more of: a total wake time after first sleep onset parameter indicative of a total time that the individual is awake in bed, after a first occurrence of falling asleep, during the time interval of interest;

a sleep onset latency parameter indicative of a total time that the individual is awake in bed, before first falling asleep, during the time interval of interest; and a number of awakenings parameter indicative of a total number of times the individual awakens from sleep during the time interval of interest.

37. A method according to claim 34 wherein determining the composite stress index based at least in part on the sleep history data, the heart beat data and the physical activity history data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index; wherein the one or more sleep parameters comprise a sleep efficiency parameter indicative of a ratio of a total time asleep while in bed to a total time in bed during the time interval of interest.

38. A method according to claim 34 wherein determining the composite stress index based at least in part on the sleep history data, the heart beat data and the physical activity history data comprises:

determining one or more sleep parameters based on the sleep history data, each sleep parameter associated with a corresponding characteristic of the individual's sleep during the time interval of interest;

determining a single-valued sleep stress index for the individual based on the one or more sleep parameters; and determining the composite stress index based at least in part on the sleep stress index; wherein the one or more sleep parameters comprise one or more of:

an average length of awake episodes parameter indicative of an average duration the individual is awake during each wake episode during the time interval of interest; and an average length of sleep episodes parameter indicative of an average duration the individual is asleep during each sleep episode during the time interval of interest.

39. A method according to claim 34 wherein the sleep history data comprises one or more sleep onset times and one or more awakening times for the individual during a second time interval and wherein determining the composite stress index based at least in part on the sleep history data, the heart beat data and the physical activity history data comprises:

determining a first sleep parameter associated with a corresponding characteristic of the individual's sleep based on the sleep history data during the time interval of interest;

determining a second sleep parameter associated with the corresponding characteristic of the individual's sleep based on the sleep history data during the second time interval;

comparing the first sleep parameter to the second sleep parameter to determine a difference metric therebetween; and determining the composite stress index based at least in part on the difference metric.

40. A method according to claim 28 wherein the heart beat data comprises data representative of the individual's cardiac activity during a second time interval and wherein determining the composite stress index based at least in part on both the activity history data and the heart beat data comprises:

determining a first cardiac parameter associated with a corresponding characteristic of the individual's cardiac activity based on the heart beat data during the time interval of interest;

determining a second cardiac parameter associated with the corresponding characteristic of the individual's cardiac activity based on the heart beat data during the second time interval;

comparing the first cardiac parameter to the second cardiac parameter to determine a difference metric therebetween; and determining the composite stress index based at least in part on the difference metric.

41. A method according to claim 28 wherein the physical activity data comprises data representative of the gross motor activity of the individual during a second time interval and wherein determining the composite stress index based at least in part on both the physical activity history data and the heart beat data comprises:

determining a first physical activity parameter associated with a corresponding characteristic of the individual's physical activity based on the physical activity history data during the time period of interest;

determining a second physical activity parameter associated with the corresponding characteristic of the individual's physical activity based on the physical activity history data during the second time period;

comparing the first physical activity parameter to the second physical activity parameter to determine a difference metric therebetween; and determining the composite stress index based at least in part on the difference metric.

42. A method according to claim 28 wherein determining the composite stress index based at least in part on the physical activity history data and the heart beat data comprises:

determining a first physical activity parameter based on the physical activity history data, the first physical activity parameter associated with a corresponding characteristic of the individual's physical activity during the time period of interest;

providing a population average physical activity parameter associated with the corresponding characteristic of physical activity of the population;

comparing the first physical activity parameter to the population average physical parameter to determine a difference metric therebetween; and determining the composite stress index based at least in part on the difference metric.

43. A system for determining a composite stress index for an individual comprising:

an actigraphy sensor for providing actigraphy data regarding an individual during a time interval of interest;

a heartbeat sensor for providing heart beat data, the heart beat data representative of the individual's cardiac activity during the time interval of interest;

a controller, the controller configured to provide: a sleep estimator configured to determine sleep history data for the individual during the time period of interest based at least in part on the actigraphy data, the sleep history data comprising one or more sleep onset times and one or more awakening times for the individual during the time interval of interest; and a composite stress index estimator configured to determine a quantitative composite stress index for the individual based at least in part on both the sleep history data and the heart beat data, the composite stress index representative of a general physiological stress of the individual during the time interval of interest.

44. A system for determining a composite stress index for an individual comprising:

an actigraphy sensor for providing physical activity history data regarding an individual during a time interval of interest, the physical activity history data representative of gross motor activity of the individual during the time interval of interest;

a heartbeat sensor for providing heart beat data, the heart beat data representative of the individual's cardiac activity during the time interval of interest; and a controller configured to provide a composite stress index estimator, the composite stress index estimator configured to determine a quantitative composite stress index for the individual based at least in part on both the physical activity history data and the heart beat data, the composite stress index representative of a general physiological stress of the individual during the time interval of interest.

* * * * *